United States Patent
Miyata et al.

(10) Patent No.: US 6,414,160 B1
(45) Date of Patent: Jul. 2, 2002

(54) PROCESS FOR PRODUCING 4-ALKOXYCARBONYL-2-OXAZOLIDINONE COMPOUND

(75) Inventors: Hiroyuki Miyata; Nobuya Satake; Takashi Honma; Kikuo Ataka, all of Yamaguchi (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/480,558
(22) PCT Filed: May 14, 1998
(86) PCT No.: PCT/JP98/02129
§ 371 (c)(1),
(2), (4) Date: Jan. 10, 2000
(87) PCT Pub. No.: WO99/02508
PCT Pub. Date: Jan. 21, 1999

(30) Foreign Application Priority Data

Jul. 10, 1997 (JP) .............................. 9-185150

(51) Int. Cl.[7] .................................. C07D 263/38
(52) U.S. Cl. .................................. 548/229
(58) Field of Search ........................ 548/229

(56) References Cited

FOREIGN PATENT DOCUMENTS

JP            60-34955 A   *   2/1985

* cited by examiner

*Primary Examiner*—Floyd D. Higel
*Assistant Examiner*—Ebenezer Sackey
(74) *Attorney, Agent, or Firm*—Jordan and Hamburg LLP

(57) ABSTRACT

The present invention relates to a process for producing 4-alkoxycarbonyl-2-oxazolidinone compound represented by the formula (III):

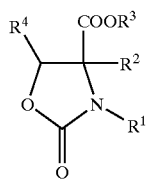

(III)

wherein $R^1$ represents H, an alkyl group, an cycloalkyl group, an alkenyl group or a phenyl group, $R^2$ represents H, an alkyl group, a phenyl group or an alkenyl group, $R^3$ represents an alkyl group, a cycloalkyl group, an alkenyl group, or a phenyl group, and $R^4$ represents H, an alkyl group, an alkenyl group, acycloalkyl group, alkynyl group, an aryl group, a 5- or 6-membered heteroaromatic ring group, an alkoxycarbonyl group, an acetyl group or a benzoyl group, which comprises reacting a 5-alkoxy-2(3H)oxazolone compound represented by the formula (I):

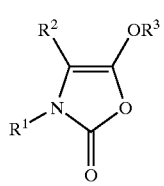

(I)

wherein $R^1$, $R^2$ and $R^3$ have the same meanings as defined above,
and an aldehyde compound represented by the formula (II):

$R^4CHO$          (II)

wherein $R^4$ has the same meaning as defined above, in the presence of a Lewis acid catalyst.

8 Claims, No Drawings

PROCESS FOR PRODUCING 4-ALKOXYCARBONYL-2-OXAZOLIDINONE COMPOUND

This application is a 371 of PCT/JP98/02129 filed on May 14, 1998.

TECHNICAL FIELD

This invention relates to a process for producing a 4-alkoxycarbonyl-2-oxazolidinone compound which is useful as synthetic starting materials or intermediates of pharmaceuticals and agricultural chemicals.

4-Alkoxycarbonyl-2-oxazolidinone compound can be easily led to a β-hydroxy-α-amino acid compound which is useful as pharmaceuticals, or pharmaceutical intermediates or starting materials in accordance with the method described in, for example, Journal of American Chemical Society, 118, pp. 3584–3590 (1996) by subjecting to alkali hydrolysis using an aqueous potassium hydroxide solution.

BACKGROUND ART

As the conventional method for preparing 4-alkoxycarbonyl-2-oxazolidinone compound, the following methods have been known.

1̂: In Nihon Kagakukai Zasshi, vol. 82, p. 1075, (1961), there is disclosed a method in which phosgene is acted on D,L-threonine in the presence of sodium hydroxide, and esterifying with methanol and hydrochloric acid to obtain 5-methyl-4-methoxycarbonyl-2-oxazoline. This method is not industrially sufficient method in the point of using β-hydroxy-α-amino acid compound which is difficultly obtained as a starting material.

2̂: In Nihon Kagakukai Zasshi, vol. 82, p. 1075, (1961), there is disclosed a method in which N-Cbz-D,L-arothreonine is subjected to ring opening in the presence of sodium hydroxide, and esterifying with methanol and hydrochloric acid to obtain 5-methyl-4-methoxycarbonyl-2-oxazolidinone. This method is also not industrially sufficient method in the point of using, as a starting material, β-hydroxy-α-amino acid compound the starting material of which is difficultly obtained.

3̂: In Journal of Organic Chemistry, vol. 44, p. 3967, (1979), there is disclosed a method in which N-carbobenzyloxyglycine ethyl ester is reacted with benzaldehyde in the presence of lithium diisopropylamide to obtain 5-phenyl-4-methoxycarbonyl-2-oxazolidinone. However, this method is not industrially satisfied preparation method in the point that lithium diisopropylamide handling of which is difficult must be used.

4̂: In Tetrahedron Letters, vol. 29, p. 2069 (1988), there is disclosed a method of obtaining 3-methyl-5-(1-methyl-3-pentenyl)-4-methoxycarbonyl-2-oxazolidinone by reacting 3-(1-methyl-3-pentenyl)-2,3-epoxy-1-propanol and methyl iso-cyanate to obtain 4-hydroxymethyloxazolidine and oxidizing the resulting compound with a chromium compound and esterifying with diazomethane. However, the method is not industrially sufficient method in the points that the steps are long and a chromium compound or diazomethane which is difficultly used industrially must be used.

Accordingly, in the above-mentioned conventionally known methods 1̂, 2̂, 3̂ and 4̂, there are problems that the starting materials are difficultly obtained, a starting material which is difficultly used for industrial purpose must be used, the steps are long and yield is low, so that a novel preparation method of 4-alkoxycarbonyl-2-oxazolidinone compound which can overcome these problems has been desired.

An object of the present invention is to provide a preparation method of a 4-alkoxycarbony-2-oxazolidinon compound which is available as a synthetic starting material or an intermediate of medicine or agricultural chemicals.

DISCLOSURE OF THE INVENTION

The present inventors have investigated to solve the above-mentioned problems and as a result, they have found that by reacting 5-alkoxy-2(3H)oxazolone compound which has not yet been described in the references and an aldehyde compound in the presence of a Lewis acid catalyst, a 4-alkoxycarbonyl-2-oxazolidinone compound can be obtained easily with high yield to accomplish the present invention. That is, the present invention is as mentioned below.

That is, the present invention related to a process for producing a 4-alkoxycarbonyl-2-oxazolidinone compound represented by the formula (III):

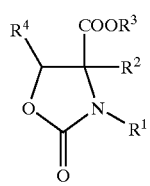

(III)

wherein $R^1$ represents a hydrogen atom, a $C_1$ to $C_{10}$ alkyl group which may be substituted, a $C_3$ to $C_{10}$ cycloalkyl group which may be substituted, a $C_2$ to $C_{10}$ alkenyl group which may be substituted or a phenyl group which may be substituted, $R^2$ represents a hydrogen atom, a $C_1$ to $C_{10}$ alkyl group which may be substituted, a phenyl group which may be substituted or a $C_2$ to $C_{10}$ alkenyl group which is not substituted, $R^3$ represents a $C_1$ to $C_{10}$ alkyl group which may be substituted, a $C_3$ to $C_{10}$ cycloalkyl group which may be substituted,o a $C_2$ to $C_{10}$ alkenyl group which may be substituted (provided that a 2-alkenyl group is excluded), or a phenyl group which may be substituted, and $R^4$ represents a hydrogen atom, a $C_1$ to $C_{20}$ alkyl group which may be substituted, a $C_2$ to $C_{20}$ alkenyl group which may be substituted, a $C_3$ to $C_{10}$ cycloalkyl group which may be substituted, a $C_2$ to $C_{20}$ alkynyl group which may be substituted, a $C_6$ to $C_{20}$ aryl group which may be substituted, a 5- or 6-membered heteroaromatic ring group having 1 or 2 hetero atoms selected from N, O and S which may be substituted, a $C_1$ to $C_6$ alkoxycarbonyl group which may be substituted, an acetyl group or a benzoyl group, which comprises reacting a 5-alkoxy-2(3H)oxazolone compound represented by the formula (I):

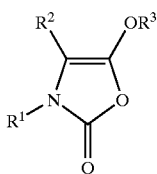

(I)

wherein $R^1$, $R^2$ and $R^3$ have the same meanings as defined above,
and an aldehyde compound represented by the formula (II):

$$R^4CHO \qquad (II)$$

wherein $R^4$ has the same meaning as defined above, in the presence of a Lewis acid catalyst to obtain the title compound.

BEST MODE FOR CARRYING OUT THE INVENTION

In the following, the present invention is explained in detail.

The process of the present invention can be shown, for example by the following reaction formula (I):

Reaction formula (I)

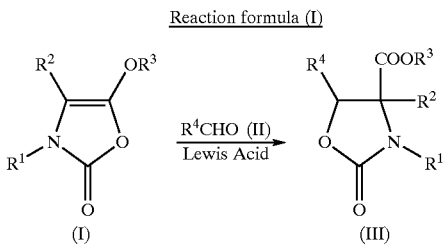

wherein $R^1$, $R^2$, $R^3$ and $R^4$ have the same meanings as defined above.

In the present invention, $R^1$ in the compound (I) represented by the formula (I) represents a hydrogen atom, a $C_1$ to $C_{10}$ alkyl group which may be substituted, a $C_3$ to $C_{10}$ cycloalkyl group which may be substituted or a $C_2$ to $C_{10}$ alkenyl group which may be substituted or a phenyl group which may be substituted.

"The $C_1$ to $C_{10}$ alkyl group which may be substituted" represented by $R^1$ means (1) "a $C_1$ to $C_{10}$ alkyl group having no substituent" or (2) "a $C_1$ to $C_{10}$ alkyl group having a substituent(s)".

As "the $C_1$ to $C_{10}$ alkyl group having no substituent" of (1), there may be mentioned, for example, a straight or branched $C_1$ to $C_{10}$ alkyl group such as a methyl group, an ethyl group, a propyl group (including an isomer), a butyl group (including isomers thereof), a pentyl group (including isomers thereof), a hexyl group (including isomers thereof), a heptyl group (including isomers thereof), an octyl group (including isomers thereof), a nonyl group (including isomers thereof) or a decyl group (including isomers thereof), etc.

As the substituent for "the $C_1$ to $C_{10}$ alkyl group having a substituent(s)", there may be mentioned, for example, a cyano group, a benzyloxy group, a phthalimino group, an acylamino group, an alkoxycarbonyl group having a straight or branched $C_1$ to $C_6$ alkyl group portion, a trialkylsilyloxy group having the same or different straight or branched $C_1$ to $C_6$ alkyl group portion, a halogen atom, an aryl group which may be substituted, "a 5- or 6-membered heteroaromatic ring group (hereinafter also referred to as "a heteroaromatic ring group") containing 1 or 2 hetero atoms selected from N, O and S", or a $C_1$ to $C_{10}$ alkoxy group which may be substituted. Incidentally, the number of the substituent(s) and the position thereof is not limited.

"The aryl group which may be substituted" as the substituent for "the $C_1$ to $C_{10}$ alkyl group having a substituent(s)" of (2) means (2-1) "an aryl group having no substituent" or (2-2) "an aryl group having a substituent(s)".

As "the aryl group having no substituent" of (2-1), there may be mentioned, for example, a phenyl group, a naphthyl group, an anthryl group or a phenanthryl group, etc.

As "the aryl group having a substituent(s)" of (2-2), there may be mentioned, for example, a nitro group; a cyano group; a benzyloxy group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; a straight or branched $C_1$ to $C_6$ alkyl group; or a straight or branched $C_1$ to $C_6$ alkoxy group. Incidentally, the number and the position of the substituent are not limited.

"The heteroaromatic ring group which may be substituted" as a substituent of "the $C_1$ to $C_{10}$ alkyl group having a substituent(s)" of (2) means (2-3) "a heteroaromatic ring group having no substituent" or (2-4) "a heteroaromatic ring group having a substituent(s)".

As (2-3) "the heteroaromatic ring group having no substituent", there may be mentioned, for example, a furyl group, a thienyl group, a pyrrolyl group, a 2H-pyrrolyl group, an oxazolyl group, an isoxazolyl group, a thiazolyl group, an isothiazolyl group, an imidazolyl group, a pyrazolyl group, a pyranyl group, a pyridyl group, a pyridazyl group, a pyrimidyl group or a pyrazinyl group, etc.

As (2-4) "the heteroaromatic ring group having a substituent(s)", there may be mentioned, for example, a nitro group; a cyano group; a benzyloxy group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; a straight or branched $C_1$ to $C_6$ alkyl group; or a straight or branched $C_1$ to $C_6$ alkoxy group. Incidentally, the number and the position of the substituent are not limited.

As (2-5) "the $C_1$ to $C_{10}$ alkoxy group having no substituent", there may be mentioned, for example, a straight or branched $C_1$ to $C_{10}$ alkoxy group such as a methoxy group, an ethoxy group, a propoxy group (including an isomer), a butoxy group (including isomers thereof), a pentyloxy group (including isomers thereof), a hexyloxy group (including isomers thereof), a heptyloxy group (including isomers thereof), an octyloxy group (including isomers thereof), a nonyloxy group (including isomers thereof) or a decyloxy group (including isomers thereof), etc.

As the substituent for (2-6) "the $C_1$ to $C_{10}$ alkoxy group having a substituent(s)", there may be mentioned, for example, a benzyloxy group; a phenoxy group; a methoxyethoxy group; a trialkylsilyloxy group having the same or different, straight or branched $C_1$ to $C_6$ alkyl group portion or a straight or branched $C_1$ to $C_6$ alkoxy group. Incidentally, the number and the position of the substituent are not limited.

"The cycloalkyl group which may be substituted" represented by $R^1$ in the compound (I) represented by the formula (I) means (3) "a $C_3$ to $C_{10}$ cycloalkyl group having no substituent" or (4) "a $C_3$ to $C_{10}$ cycloalkyl group having a substituent(s)".

As (3) "the $C_3$ to $C_{10}$ cycloalkyl group having no substituent", there may be mentioned, for example, a $C_3$ to $C_{10}$ cycloalkyl group such as a cyclopropyl group, a cyclobutyl group, a cyclopentyl group, a cyclohexyl group, a cycloheptyl group, a cyclooctyl group, a cyclononyl group, a cyclodecyl group, a bornyl group or an adamantyl group, etc.

As the substituent for (4) "the $C_3$ to $C_{10}$ cycloalkyl group having a substituent(s)", there may be mentioned, for example, a cyano group; a benzyloxy group; a benzosulfonyl group; an acylamino group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; a straight or branched $C_1$ to $C_6$ alkyl group; an aryl group which may be substituted or a straight or branched $C_1$ to $C_6$ alkoxy group. Incidentally, the number and the position of the substituent are not limited.

"The $C_2$ to $C_{10}$ alkenyl group which may be substituted" represented by $R^1$ in the compound (I) represented by the formula (I) has the same meanings as (5) "a $C_2$ to $C_{10}$ alkenyl group having no substituent" or (6) "a $C_2$ to $C_{10}$ alkenyl group having a substituent(s)".

As (5) "the $C_2$ to $C_{10}$ alkenyl group having no substituent", there may be mentioned, for example, a straight or branched $C_2$ to $C_{10}$ alkenyl group such as an ethenyl group, a propenyl group (including its isomer), a butenyl group (including isomers thereof), a pentenyl group (including isomers thereof), a hexenyl group (including isomers thereof), a heptenyl group (including isomers thereof), an octenyl group (including isomers thereof), a nonenyl group (including isomers thereof) or a decenyl group (including isomers thereof), etc.

As the substituent for (6) "the $C_2$ to $C_{10}$ alkenyl group having a substituent(s)", there may be mentioned, for example, a cyano group; a benzyloxy group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; an aryl group which may be substituted; a heteroaromatic ring group which may be substituted or a straight or branched $C_1$ to $C_6$ alkoxy group. Incidentally, the number of the substituent and the position thereof are not particularly limited.

"The phenyl group which may be substituted" represented by $R^1$ in the compound (I) represented by the formula (I) means a phenyl group or "a phenyl group having a substituent(s)". As the substituent for "the phenyl group having a substituent(s)", there may be mentioned, for example, a straight or branched $C_1$ to $C_6$ alkyl group, a nitro group, a benzyloxy group, a halogen atom, an acylamino group and a straight or branched $C_1$ to $C_6$ alkoxy group. Incidentally, the number and the position of the substituent (s) are not limited.

Specific examples of such $R^1$ may include, for example, a hydrogen atom, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-cyanoethyl group, a 1-methoxycarbonylethyl group, a 2-trimethylsilyloxyethyl group, a 2-benzyloxyethyl group, a 2-trifluoroethyl group, a 2-chloroethyl group, a benzyl group, a 4-nitrobenzyl group, a cyanobenzyl group, a 4-methoxycarbonylbenzyl group, a 4-trimethysilyloxybenzyl group, a 4-benzyloxybenzyl group, a 3,4-difluorobenzyl group, a 4-methylbenzyl group, an 2-methylbenzyl group, a 3,4-dichlorobenzyl group, an 2-fluorobenzyl group, a 4-fluorobenzyl group, a 2,4-dimethylbenzyl group, a 4-isopropylbenzyl group, a 4-tert-butylbenzyl group, an 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a 1-phenylethyl group, a 1-(4-nitrophenyl)ethyl group, a 1-(4-bromophenyl)ethyl group, a 1-(4-fluorophenyl)ethyl group, a 1-(4-methoxyphenyl)ethyl group, a 1-(4-chlorophenyl)ethyl group, a 1-(1-naphthyl)ethyl group, a 1-(2-naphthyl)ethyl group, a diphenylmethyl group, a di(4-chlorophenyl)methyl group, a di(4-methoxyphenyl)methyl group, a trityl group, a 1-(2-phenanthryl)ethyl group, a 1-(9-anthranyl)ethyl group, a furfuryl group, a 2-thienylmethyl group, a 2-pyridylmethyl group, a 3-pyridylmethyl group, an isothiazolylmethyl group, a 2-pyrazolylethyl group, a (2H-pyrrolyl) group, an (N-methylpyrrolyl)methyl group, an isoxazolylmethyl group, a 2-methyoxyethyl group, a 2-ethoxyethyl group, a 2-(n-propoxy)ethyl group, a 2-isopropoxyethyl group, a 3-(n-butoxy)propyl group, 2-(sec-butoxy)ethyl group, a 2-(tert-butoxy)ethyl group, a 2-hexyloxyethyl group, a 2-methoxy-n-butyl group, a 2-(tert-butoxy)-1,1-dimethylethyl group, a 2-octyloxyethyl group, a 2-nonyloxyethyl group, a 2-heptyloxyethyl group, a 2-methoxyethoxyethyl group, a 2-(benzyloxymethoxy)-ethyl group, a 2-(2-methoxyethoxymethoxy)ethyl group, a 2-(ethoxymethoxy)-ethyl group, a 2-(phenoxymethoxy)-ethyl group, a 2-formaminoethyl group, a 2-acetaminoethyl group, a 2-chloroacetaminoethyl group, a 2-benzoylaminoethyl group, a 2-phenylacetaminoethyl group, a 2-methoxycarbonylaminoethyl group, a 2-ethoxycarbonylaminoethyl group, a 2-allyloxycarbonylaminoethyl group, a 2-tert-butoxycarbonylaminoethyl group, a 2-benzyloxycarbonylaminoethyl group, an ethynyl group, a propenyl group, a butenyl group, a pentenyl group, a hexenyl group, a heptenyl group, an octenyl group, a nonenyl group, a decenyl group, a 2-cyanoethynyl group, a 1-methoxycarbonyl-2-propenyl group, a 1-trimethylsilyloxymethyl-2-propenyl group, a 1-benzyloxymethyl-2-propenyl group, a cinnamyl group, a 2-methoxymethyl-2-propenyl group, a 2-ethoxymethyl-2-propenyl group, a cyclopropyl group, a cyclobutyl group, a cyclopentyl group, a cyclohexyl group, a cycloheptyl group, a cyclooctyl group, a cyclononyl group, a cyclodecyl group, a 1-methoxycarbonylcyclopropyl group, a 2-phenylcyclopropyl group, a 2-fluorocyclopropyl group, a 2-chlorocyclopropyl group, a 2-benzyloxycyclopropyl group, a 1-cyanocyclopentyl group, a 2-norbornyl group, a bornyl group, a 1-adamanthyl group, a 4-methylcyclohexyl group, a 2-methylcyclohexyl group, a 2,3-dimethylcyclohexyl group, a 2-methoxycarbonylcyclohexyl group, a 2-methoxycyclohexyl group, a 2-trimethylsilyloxycyclohexyl group, a 2-benzyloxycyclohexyl group, a 4-benzyloxycyclohexyl group, 4-tert-butylcyclohexyl group, a menthyl group, a 8-phenylmenthyl group, a phenyl group, a 2-methylphenyl group, a 3-methylphenyl group, a 4-methylphenyl group, a 4-tert-butylphenyl group, a 3,4-dimethylphenyl group, a 4-ethylphenyl group, a 2-chlorophenyl group, a 3-chlorophenyl group, a 4-chlorophenyl group, a 2-fluorophenyl group, a 3-fluorophenyl group, a 4-fluorophenyl group, a 2-bromophenyl group, a 3-bromophenyl group, a 4-bromophenyl group, a 2-iodophenyl group, a 4-iodophenyl group, a 4-methoxyphenyl group, a 3,4-dimethoxyphenyl group, a 3,4-dibenzyloxyphenyl group, a 4-benzyloxyphenyl group, a 2-benzyloxyphenyl group, a 2-methoxyphenyl group, a 3-methoxyphenyl group and a 4-nitrophenyl group, etc.

In the present invention, $R^2$ in the compound (I) represented by the formula (I) represents a hydrogen atom, a $C_1$ to $C_{10}$ alkyl group which may be substituted, a phenyl group which may be substituted or a $C_2$ to $C_{10}$ alkenyl group which is not substituted.

"The $C_1$ to $C_{10}$ alkyl group which may be substituted" represented by $R^2$ means (7) "a $C_1$ to $C_{10}$ alkyl group having no substituent" or (8) "a $C_1$ to $C_{10}$ alkyl group having a substituent(s)".

As "the $C_1$ to $C_{10}$ alkyl group having no substituent" of (7) may be mentioned, for example, the above-mentioned straight or branched $C_1$ to $C_{10}$ alkyl group.

As the substituent of (8) "the $C_1$ to $C_{10}$ alkyl group having a substituent(s)", there may be mentioned, for example, a phthalimide group; a benzyloxy group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; an aryl group which may be substituted; a heteroaromatic ring group which may be substituted; a straight or branched $C_1$ to $C_{10}$ alkoxy group; an acylamino group; a $C_1$ to $C_{10}$ alkylthio group or a benzylthio group. Incidentally, the number and the position of the substituent are not limited.

"The aryl group which may be substituted" as a substituent for (8) "the $C_1$ to $C_{10}$ alkyl group having a substituent (s)" means (8-1) "an aryl group having no substituent" or (8-2) "an aryl group having a substituent(s)".

As (8-1) "the aryl group having no substituent", there may be mentioned, for example, a phenyl group or a naphthyl group.

As the substituent for (8-2) "the aryl group having a substituent(s)", there may be mentioned, for example, a straight or branched $C_1$ to $C_6$ alkyl group; a nitro group; a benzyloxy group; a cyano group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; an acylamino group or a straight or branched $C_1$ to $C_6$ alkoxy group. Incidentally, the number and the position of the substituent are not limited.

"The heteroaromatic ring group which may be substituted" as a substituent for (8) "the $C_1$ to $C_{10}$ alkyl group having a substituent(s)" means (8-3) "a heteroaromatic ring group having no substituent" or (8-4) "a heteroaromatic ring group having a substituent(s)".

As (8-3) "the heteroaromatic ring group having no substituent", there may be mentioned, for example, a furyl group, a thienyl group, an oxazolyl group, an isoxazolyl group, a thiazolyl group, an indolyl group or an imidazolyl group, etc.

The heteroaromatic ring group of (8-4) "the heteroaromatic ring group having a substituent (s)" has the same meaning as (8-3) "the heteroaromatic ring group having no substituent". As the substituent for (8-4) "the heteroaromatic ring group having a substituent (s)", there may be mentioned, for example, a straight or branched $C_1$ to $C_{10}$ alkyl group; a halogen atom or an alkoxycarbonyl group having a straight or branched $C_1$ to $C_6$ alkyl group portion. Incidentally, the number and the position of the substituent are not limited.

In the present invention, "the phenyl group which may be substituted" represented by $R^2$ in the compound (I) represented by the formula (I) means a phenyl group or "a phenyl group having a substituent(s)". As the substituent for "the phenyl group having a substituent(s)", there may be mentioned, for example, a benzyloxy group, a halogen atom, a straight or branched $C_1$ to $C_6$ alkoxy group; an acylamino group or a trialkylsilyloxy group having the same or different, straight or branched $C_1$ to $C_6$ alkyl group portion, etc. Incidentally, the number and the position of the substituent(s) are not limited.

In the present invention, "the $C_2$ to $C_{10}$ alkenyl group which is not substituted" represented by $R^2$ in the compound (I) represented by the formula (I) may be mentioned, for example, a straight or branched $C_2$ to $C_{10}$ alkenyl group.

Specific examples of such $R^2$ may include, for example, a hydrogen atom, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-methoxycarbonylethyl group, a 3-methoxycarbonylpropyl group, a 4-methoxycarbonylbutyl group, a 1-trimethylsilyloxyethyl group, a benzyloxymethyl group, a 1-benzyloxyethyl group, a 1-benzyloxypropyl group, a 1-benzyloxybutyl group, a methoxymethyl group, a 1-tert-butoxyethyl group, a 1-ethoxyethyl group, a 1-hexyloxyethyl group, an isopropoxymethyl group, a n-propoxymethyl group, a 2-methylthioethyl group, a 2-ethylthioethyl group, a methylthiomethyl group, a butylthiomethyl group, a tert-butylthiomethyl group, a benzylthiomethyl group, a 2-trifluoroethyl group, a trifluoromethyl group, a 2-chloroethyl group, a fluoromethyl group, a 1-fluorobutyl group, a 1-fluoro-1-phenylmethyl group, a 1-fluoroethyl group, a 2-acetylaminoethyl group, a 3-benzoylaminopropyl group, a 4-formylaminobutyl group, a 4-acetylaminobutyl group, a 4-chloroacetaminobutyl group, a 4-phenylacetaminobutyl group, a 4-methoxycarbonylaminobutyl group, a 4-ethoxycarbonylaminobutyl group, a 4-allyloxycarbonylaminobutyl group, a 4-tert-butyloxycarbonylaminobutyl group, a 4-benzyloxycarbonyl-aminobutyl group, a 4-phthaloylaminobutyl group, a benzyl group, a 4-nitrobenzyl group,-a 4-cyanobenzyl group, a 4-methoxycarbonylbenzyl group, a 4-trimethylsilyloxybenzyl group, a 4-benzyloxybenzyl group, a 3,4-dichlorobenzyl group, a 2-fluorobenzyl group, a 4-fluorobenzyl group, a 3,4-difluorobenzyl group, a 4-methylbenzyl group, a 2-methylbenzyl group, a 2,4-dimethylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a 4-tert-butoxycarbonylaminobenzyl group, a 4-acetylaminobenzyl group, a 2-benzyloxycarbonylaminobenzyl group, a 1-phenylethyl group, a 1-(4-nitrophenyl) ethyl group, a 1-(4-bromophenyl) ethyl group, a 1-(4-fluorophenyl)ethyl group, a 1-(4-methoxyphenyl)ethyl group, a 1-(4-chlorophenyl)ethyl group, a 1-(1-naphthyl)ethyl group, a 1-(2-naphthyl)ethyl group, a diphenylmethyl group, a di(4-chlorophenyl)methyl group, a di(4-methoxyphenyl) methyl group, a trityl group, a 2-phenylethyl group, a 2-(4-benzyloxyphenyl)ethyl group, a furfuryl group, a thienylmethyl group, a thiazolylmethyl group, an isoxazolylmethyl group, an oxazolylmethyl group, a (4-N-methylimidazolyl)methyl group, an N-methylindolylmethyl group, a phenyl group, a 2-fluorophenyl group, a 4-benzyloxyphenyl group, a 4-methoxyphenyl group, a 2-chlorophenyl group, a 4-bromophenyl group, a 4-acetaminophenyl group, a 4-benzyloxycarbonylaminophenyl group, an ethynyl group, a 1-propenyl group, a 2-propenyl group, a 1-butenyl group, a 2-butenyl group, a 3-butenyl group, a 1-pentenyl group, a 2-pentenyl group, a hexenyl group, a heptenyl group, an octenyl group, a nonenyl group or a decenyl group.

In the present invention, $R^3$ in the compound (I) represented by the formula (I) represents a $C_1$ to $C_{10}$ alkyl group which may be substituted, a $C_3$ to $C_{10}$ cycloalkyl group which may be substituted, a $C_2$ to $C_{10}$ alkenyl group which may be substituted (provided that a 2-alkenyl group is excluded) or a phenyl group which may be substituted.

"The $C_1$ to $C_{10}$ alkyl group which may be substituted" represented by $R^3$ in the compound (I) represented by the formula (I) means (9) "a $C_1$ to $C_{10}$ alkyl group having no substituent" or (10) "a $C_1$ to $C_{10}$ alkyl group having a substituent(s)".

As (9) "the $C_1$ to $C_{10}$ alkyl group having no substituent", there may be mentioned, for example, the above-mentioned straight or branched $C_1$ to $C_{10}$ alkyl group.

As the substituent for (10) "the $C_1$ to $C_{10}$ alkyl group having a substituent(s)", there may be mentioned, for example, a benzyloxy group; an alkoxycarbonyl group having a straight or branched $C_1$ to $C_6$ alkyl group portion; an acylamino group; a halogen atom; "the aryl group which may be substituted" as "mentioned in (8-1) and (8-2)" or a $C_1$ to $C_{10}$ alkoxy group as "mentioned in (2-5)".

"The $C_3$ to $C_{10}$ cycloalkyl group which may be substituted" represented by $R^3$ in the formula (I) represented by the formula (I) means (11) "a $C_3$ to $C_{10}$ cycloalkyl group having no substituent" or (12) "a $C_3$ to $C_{10}$ cycloalkyl group having a substituent(s)".

(11) "The $C_3$ to $C_{10}$ cycloalkyl group having no substituent" has the same meaning as "the $C_3$ to $C_{10}$ cycloalkyl group having no substituent" mentioned in (3), and (12) "the $C_3$ to $C_{10}$ cycloalkyl group having a substituent(s)" have the same meaning as "the $C_3$ to $C_{10}$ cycloalkyl group having a substituent(s) mentioned in (4).

"The $C_2$ to $C_{10}$ alkenyl group which may be substituted (provided that a 2-alkenyl group is excluded)" represented by $R^3$ in the formula (I) represented by the formula (I) means (13) "a $C_2$ to $C_{10}$ alkenyl group having no substituent (provided that a 2-alkenyl group is excluded) or (14) "a $C_2$ to $C_{10}$ alkenyl group having a substituent(s) (provided that a 2-alkenyl group is excluded)".

As (13) "the $C_2$ to $C_{10}$ alkenyl group having no substituent (provided that a 2-alkenyl group is excluded)", there may be mentioned, for example, a straight or branched $C_2$ to $C_{10}$ alkenyl group having no substituent (provided that a 2-alkenyl group is excluded)".

Incidentally, when the process represented by the reaction formula (I) of the present invention as mentioned below is carried out by using a compound represented by the formula (II) containing a 2-alkenyl group in the molecule as $R^3$, the compound represented by the formula (I) cannot be obtained.

As (14) "the $C_2$ to $C_{10}$ alkenyl group having a substituent(s) (provided that a 2-alkenyl group is excluded)", there may be mentioned, for example, a benzyloxy group; an alkoxycarbonyl group having a straight or branched $C_1$ to $C_6$ alkyl group portion; an acylamino group; a halogen atom; an aryl group which may be substituted "as mentioned in (8-1) and (8-2)" or a $C_1$ to $C_{10}$ alkoxy group "as mentioned in (2-5)". Incidentally, the number and the position of the substituent(s) are not limited.

"The phenyl group which may be substituted" represented by $R^3$ in the compound (I) represented by the formula (I) means a phenyl group or "a phenyl group having a substituent(s)". As the substituent for "the phenyl group having a substituent(s)", there may be mentioned, for example, a straight or branched $C_1$ to $C_6$ alkyl group, a nitro group, and the above-mentioned halogen atom.

Specific examples of such $R^3$ may include, for example, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a 2-methoxycarbonylethyl group, a 3-methoxycarbonylpropyl group, a 4-methoxycarbonylbutyl group, a 1-benzyloxyethyl group, a 3-benzyloxypropyl group, a 3-benzyloxyisobutyl group, a 2-methoxyethyl group, a 2-tert-butoxyethyl group, a 2-ethoxyethyl group, a 2-hexyloxyethyl group, a 2-isopropoxyethyl group, a 3-n-propoxypropyl group, a 2-trifluoroethyl group, a trifluoromethyl group, a 2-chloroethyl group, a fluoromethyl group, a 2-fluoroethyl group, a 1-fluorobutyl group, a 1-fluoro-1-phenylmethyl group, a 1-fluoroethyl group, a 2-bromoethyl group, a 2-acetylaminoethyl group, a 3-benzoylaminopropyl group, a 4-formylaminobutyl group, a 4-acetylaminobutyl group, a 4-chloroacetaminobutyl group, a 4-phenylacetaminobutyl group, a 4-methoxycarbonylaminobutyl group, a 4-ethoxycarbonylaminobutyl group, a 4-allyloxycarbonylaminobutyl group, a 4-tert-butyloxycarbonylaminobutyl group, a 4-benzyloxycarbonylaminobutyl group, a benzyl group, a 4-nitrobenzyl group, a 4-trimethylsilyloxybenzyl group, a 4-benzyloxybenzyl group, 3,4-dichlorobenzyl group, a 2-fluorobenzyl group, a 4-fluorobenzyl group, a 3,4-difluorobenzyl group, a 4-methylbenzyl group, a 2-methylbenzyl group, a 2,4-dimethylbenzyl group, a 4-isopropylbenzyl group, a 4-tert-butylbenzyl group, a 2-methoxybenzyl group, a 3-methoxybenzyl group, a 4-methoxybenzyl group, a 3,4-dimethoxybenzyl group, a 2,4-dimethoxybenzyl group, a 2-ethoxybenzyl group, a 4-isopropoxybenzyl group, a 4-tert-butoxybenzyl group, a 4-tert-butoxycarbonylaminobenzyl group, a 4-acetylaminobenzyl group, a 2-benzyloxycarbonylbenzyl group, a 1-phenylethyl group, a 1-(4-nitrophenyl)ethyl group, a 1-(4-bromophenyl)ethyl group, a 1(4-fluorophenyl) ethyl group, a 1-(4-methoxyphenyl)ethyl group, a 1-(4-chlorophenyl)ethyl group, a 1-(1-naphthyl)ethyl group, a 1(2-naphthyl)ethyl group, a diphenylmethyl group, a di(4-chlorophenyl)methyl group, a di(4-methoxyphenyl)methyl group, a trityl group, a 2-phenylethyl group, a 2-(4-benzyloxyphenyl)ethyl group, an ethenyl group, a 1-propenyl group, a 1-butenyl group, a 3-butenyl group, a 1-pentenyl group, a 3-pentenyl group, a 4-pentenyl group, a 5-hexenyl group, a 6-heptenyl group, a 7-octenyl group, a 8-nonyl group, a 9-decenyl group, a 3-methoxycarbonyl-1-propenyl group, a 1-methoxycarbonylethynyl group, a 2-benzyloxymethylethynyl group, a 3-chloro-4-pentenyl group, a 4-chloro-3-butenyl group, a 4-phenyl-3-butenyl group, a 5-phenyl-4-pentenyl group, a 5-benzyloxy-3-butenyl group, a 6-methoxy-3-hexenyl group, a cyclopropyl group, a cyclobutyl group, a cyclopentyl group, a cyclohexyl group, a cycloheptyl group, a cyclooctyl group, a cyclononyl group, a cyclodecyl group, a 1-methoxycarbonylcyclopropyl group, a 2-phenylcyclopropyl group, a 2-fluorocyclopropyl group, a 2-chlorocyclopropyl group, a 1-benzyloxymethylcyclopentyl group, a 3-cyanocyclopentyl group, a 2-acetaminocyclohexyl group, a 2-benzoylaminocyclohexyl group, a 2-methoxycarbonylaminocyclohexyl group, a 2-tert-butoxycarbonylaminocyclohexyl group, a 2-benzyloxycarbonylaminocyclohexyl group, a 2-methoxycyclohexyl group, a 2-chlorocyclohexyl group, a 2-norbornyl group, a bornyl group, a 2-adamantyl group, an N-benzosulfonyl-N-(3,5-dimethylphenyl)-aminobornyl group, a 4-methylcyclohexyl group, a 2-methyl-cyclohexyl group, a 2,3-dimethylcyclohexyl group, a 1-methoxycarbonylcyclohexyl group, a 2-trimethylsiloxycyclohexyl group, a 2-benzyloxycyclohexyl group, a 4-benzyloxycyclohexyl group, a 4-tert-butylcyclohexyl group, a menthyl group, a 8-phenylmenthyl group, a phenyl group, a 2-methylphenyl group, a 4-methylphenyl group, a 2,5-di-tert-butyl-4-methyl group, a 4-tert-butyl group, a 2-chlorophenyl group, a 4-chlorophenyl group, a 4-fluorophenyl group, a 2-fluorophenyl group, a 3-chlorophenyl group or a 4-nitrophenyl group, etc.

As the specific compounds of the compound (I) represented by the formula (I), there may be mentioned, for example, 3-benzyl-5-methoxy-2(3H)oxazolone, 3-benzyl-4-methyl-5-methoxy-2(3H)oxazolone, 3-(4-nitrobenzyl)-5-ethoxy-2(3H)oxazolone, 3-benzyl-5-(l)-menthyloxy-2(3H)oxazolone, 3-(4-methylbenzyl)-4-methyl-5-methoxy-2(3H)oxazolone, 3-(1-phenylethyl)-5-methoxy-2(3H)oxazolone, 3-((S)-1-phenylethyl)-5-isopropoxy-2(3H)oxazolone, 3-((R)-1-phenylethyl)-5-methoxy-2(3H)oxazolone, 3-diphenylmethyl-5-methoxy-2(3H)oxazolone, 3-diphenylmethyl-4-methyl-5-methoxy-2(3H)oxazolone, 3-diphenylmethyl-5-(l)-menthyloxy-2(3H)oxazolone, 3-diphenylmethyl-5-((1S,2S,5R)-5-methyl-2-(1-methyl-1-phenylethyl)cyclohexyl-oxy)-2(3H)oxazolone, 3-benzyl-5-((1S,2S,5R)-5-methyl-2-(1-methyl-1-phenylethyl) cyclohexyloxy)-2(3H)oxazolone, 3-diphenylmethyl-4-isopropyl-5-isopropoxy-2(3H)oxazolone, 3-diphenylmethyl-4-phenylmethyl-5-methoxy-2(3H) oxazolone, 3-diphenylmethyl-4-isobutyl-5-ethoxy-2(3H) oxazolone, 3-diphenylmethyl-4-(sec-butyl)-5-methoxy-2 (3H)oxazolone, 3-diphenylmethyl-4-(benzyloxyphenyl)-5-methoxy-2(3H)oxazolone, 3-diphenylmethyl-4-methoxycarbonylmethyl-5-isopropoxy-2(3H)oxazolone, 3-diphenylmethyl-4-benzyloxymethyl-5-methoxy-2(3H) oxazolone, 3-diphenylmethyl-4-(2-methoxycarbonylethyl)-5-methoxy-2(3H)oxazolone, 3-diphenylmethyl-4-(4-BocNH-butyl)-5-methoxy-2(3H)oxazolone (Boc=tert-butoxy-carbonyl), 3-(1-(1-naphthyl)ethyl)-4-isopropyl-5-isopropoxy-2(3H)oxazolone, 3-(1-(1-naphthyl)ethyl)-4-phenylmethyl-5-methoxy-2(3H)oxazolone, 3-(1-(1-naphthyl)ethyl)-4-isobutyl-5-ethoxy-2(3H)oxazolone, 3-(1-(1-naphthyl)ethyl)-4-(sec-butyl)-5-methoxy-2(3H) oxazolone, 3-(1-(1-naphthyl)ethyl)-4-(benzyloxyphenyl)-5-methoxy-2(3H)oxazolone, 3-(1-(1-naphthyl)ethyl)-4-methoxycarbonylmethyl-5-isopropoxy-2(3H)oxazolone, 3-(1-(1-naphthyl)ethyl)-4-benzyloxymethyl-5-methoxy-2 (3H)oxazolone, 3-(1-(1-naphthyl)ethyl)-4-(2-methoxycarbonylethyl)-5-methoxy-2(3H)oxazolone, 3-(1-(1-naphthyl)ethyl)-4-(4-BocNH-butyl)-5-methoxy-2(3H) oxazolone, 3-(1-phenylethyl)-4-isopropyl-5-methoxy-2(3H) oxazolone, 3-(1-phenylethyl)-4-phenylmethyl-5-methoxy-2 (3H)oxazolone, 3-(1-phenylethyl)-4-isobutyl-5-ethoxy-2 (3H)oxazolone, 3-(1-phenylethyl)-4-(sec-butyl)-5-methoxy-2(3H)oxazolone, 3-(1-phenylethyl)-4-(benzyloxyphenyl)-5-methoxy-2(3H)oxazolone, 3-(1-phenylethyl)-4-methoxycarbonylmethyl-5-ethoxy-2(3H)oxazolone, 3-(1-phenylethyl)-4-benzyloxymethyl-5-methoxy-2(3H)-oxazolone, 3-(1-phenylethyl)-4-(2-methoxycarbonylethyl)-5-methoxy-2(3H)oxazolone, 3-(1-phenylethyl)-4-(4-BocNH-butyl)-5-methoxy-2(3H)oxazolone, 3-((R)-1-(1-naphthyl)ethyl)-5-methoxy-2(3H)oxazolone, 3-furfuryl-4-ethyl-5-methoxy-2(3H)-oxazolone, 3-furfuryl-4-ethyl-5-(4-pentenyl)oxy-2(3H)oxazolone, 3-isopropyl-5-methoxy-2 (3H)oxazolone, 3-benzyl-5-methoxy-2(3H)oxazolone, 3-isopropyl-4-methyl-5-methoxy-2(3H)oxazolone, 3-isopropyl-4-methyl-5-ethoxy-2(3H)oxazolone, 3-isopropyl-4-methyl-5-cyclohexyloxy-2(3H)oxazolone, 3-methyl-5-isopropoxy-2(3H)oxazolone, 3-((R)-1-(1-naphthyl)-ethyl)-5-isopropoxy-2(3H)oxazolone, 3-((R)-1-phenylethyl)-4-methyl-5-methoxy-2(3H)oxazolone, 3-((S)-1-phenylethyl)-5-phenoxy-2(3H)oxazolone, 3-diphenylmethyl-4-methyl-5-phenoxy-2(3H)oxazolone, 3-phenyl-4-methyl-5-methoxy-2(3H)oxazolone, 3-(p-chlorophenyl)-4-ethyl-5-methoxy-2(3H)oxazolone, 3-(o-chlorophenyl)-4-methyl-5-methoxy-2(3H)oxazolone, 3-(3, 4-dimethoxyphenyl)-4-methyl-5-methoxy-2(3H)oxazolone and 3-phenyl-5-methoxy-2(3H)oxazolone, etc.

The 5-alkoxy-2(3H)oxazolone (Compound (I)) represented by the formula (I) of the present invention can be produced according to the method of the reaction formula (2) as mentioned below. (Reaction formula 2)

(Reaction formula 2)

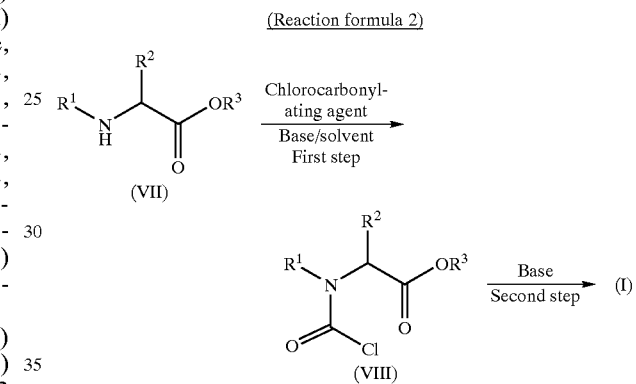

wherein $R^1$, $R^2$ and $R^3$ have the same meanings as defined above.

The first step is to produce a compound represented by the formula (VIII) (hereinafter also referred to as Compound (VIII), and can be accomplished by reacting an N-substituted-α-amino acid ester compound represented by the formula (VII) (hereinafter also referred to as Compound (VII)) with a chlorocarbonylating agent such as phosgene, trichloromethyl chloroformate, etc. in the presence of an inorganic base such as sodium carbonate, etc., or an organic base such as triethylamine, etc., or the like in a solvent.

The second step is to produce a compound represented by the formula (I), and the compound (I) can be obtained by subjecting the compound represented by the formula (VIII) to intramolecular cyclization reaction in the presence of an organic base such as triethylamine or tri-n-propylamine, etc., or an inorganic base such as sodium carbonate, etc.

In the present invention, $R^4$ in the compound (II) represented by the formula (II) represents a hydrogen atom, a $C_1$ to $C_{20}$ alkyl group which may be substituted, a $C_2$ to $C_{20}$ alkenyl group which may be substituted, a $C_3$ to $C_{10}$ cycloalkyl group which may be substituted, a $C_2$ to $C_{20}$ alkynyl group which may be substituted, a $C_6$ to $C_{20}$ aryl group which may be substituted, a 5- or 6-membered heteroaromatic ring group containing 1 or 2 hetero atoms selected from N, O and S, which may be substituted, a $C_1$ to $C_6$ alkoxycarbonyl group which may be substituted, an acetyl group or a benzoyl group.

"The $C_1$ to $C_{20}$ alkyl group which may be substituted" represented by $R^4$ means (15) "a $C_1$ to $C_{20}$ alkyl group having no substituent" or (16) "a $C_1$ to $C_{20}$ alkyl group having a substituent(s)".

As (15) "the $C_1$ to $C_{20}$ alkyl group having no substituent", there may be mentioned, for example, a straight or branched $C_1$ to $C_{20}$ alkyl group such as a methyl group, an ethyl group, a propyl group (including an isomer), a butyl group (including isomers thereof), a pentyl group (including isomers thereof), a hexyl group (including isomers thereof), a heptyl group (including isomers thereof), an octyl group (including isomers thereof), a nonyl group (including isomers thereof), a decyl group (including isomers thereof), an undecyl group (including isomers thereof), a dodecyl group (including isomers thereof), a tridecyl group (including isomers thereof), a tetradecyl group (including isomers thereof), a pentadecyl group (including isomers thereof), a hexadecyl group (including isomers thereof), a heptadecyl group (including isomers thereof), an octadecyl group (including isomers thereof), a nonadecyl group (including isomers thereof) or an eicosyl group (including isomers thereof), etc.

As the substituent for (16) "the $C_1$ to $C_{20}$ alkyl group having a substituent(s)", there may be mentioned, for example, a cyano group; a benzyloxy group; a phthalimino group; an alkoxycarbonyl group having a straight or branched $C_1$ to $C_6$ alkyl group portion; a trialkylsilyloxy group having the same or different straight or branched $C_1$ to $C_6$ alkyl group portion; an acylamino group; a halogen atom; an aryl group as "described in (2-1) and (2-2)"; a heteroaromatic ring group as "described in (8-3) and (8-4)" or a $C_1$ to $C_{10}$ alkoxy group as "described in (2-5) and (2-6)".

"The $C_2$ to $C_{20}$ alkenyl group which may be substituted" represented by $R^4$ in the compound (II) represented by the formula (II) has the same meaning as (17) "a $C_2$ to $C_{20}$ alkenyl group having no substituent" or (18) "a $C_2$ to $C_{20}$ alkenyl group having a substituent(s)".

As (17) "the $C_2$ to $C_{20}$ alkenyl group having no substituent", there may be mentioned, for example, a straight or branched $C_2$ to $C_{20}$ alkenyl group.

As the substituent for (18) "the $C_2$ to $C_{20}$ alkenyl group having a substituent(s)", there may be mentioned, for example, a cyano group; a benzyloxy group; an acylamino group; an alkoxycarbonyl group having a straight or branched $C_1$ to $C_6$ alkyl group portion; a trialkylsilyloxy group having the same or different straight or branched $C_1$ to $C_6$ alkyl group portion; a halogen atom; an aryl group as "described in (2-3) and (2-4)"; a $C_3$ to $C_{10}$ cycloalkyl group or a heteroaromatic ring group.

"The $C_3$ to $C_{10}$ cycloalkyl group which may be substituted" represented by $R^4$ in the compound (II) represented by the formula (II) has the same meaning as (19) "a $C_3$ to $C_{10}$ cycloalkyl group having no substituent" or (20) "a $C_3$ to $C_{10}$ cycloalkyl group having a substituent(s)".

As (19) "the $C_3$ to $C_{10}$ cycloalkyl group having no substituent", there may be mentioned, for example, a cyclopropyl group, a cyclobutyl group, a cyclopentyl group, a cyclohexyl group, a cycloheptyl group, a cyclooctyl group, a cyclononyl group or a cyclodecyl group.

As the substituent for (20) "the $C_3$ to $C_{10}$ cycloalkyl group having a substituent(s)", there may be mentioned, for example, a cyano group; a benzyloxy group; an alkoxycarbonyl group having a straight or branched $C_1$ to $C_6$ alkyl group portion; a trialkylsilyloxy group having the same or different straight or branched $C_1$ to $C_6$ alkyl group portion; an acylamino group; a halogen atom; an aryl group or a $C_1$ to $C_6$ alkoxy group. Incidentally, the number and the position of the substituent(s) are not limited.

"The $C_2$ to $C_{20}$ alkynyl group which may be substituted" represented by $R^4$ in the compound (II) represented by the formula (II) has the same meaning as (21) "a $C_2$ to $C_{20}$ alkynyl group having no substituent" or (22) "a $C_2$ to $C_{20}$ alkynyl group having a substituent(s)".

As (21) "the $C_2$ to $C_{20}$ alkynyl group having no substituent", there may be mentioned, for example, a straight or branched $C_2$ to $C_{20}$ alkynyl group.

As the substituent for (22) "the $C_2$ to $C_{20}$ alkynyl group having a substituent(s)", there may be mentioned, for example, a cyano group; a benzyloxy group; an acylamino group; an alkoxycarbonyl group having a straight or branched $C_1$ to $C_6$ alkyl group portion; a trialkylsilyloxy group having the same or different straight or branched $C_1$ to $C_6$ alkyl group portion; a halogen atom or an aryl group.

"The $C_6$ to $C_{20}$ aryl group which may be substituted" represented by $R^4$ in the compound (II) represented by the formula (II) has the same meaning as (23) "a $C_6$ to $C_{20}$ aryl group having no substituent" or (24) "a $C_6$ to $C_{20}$ aryl group having a substituent(s)".

As (23) "the $C_6$ to $C_{20}$ aryl group having no substituent", there may be mentioned, for example, a phenyl group, a naphthyl group, an anthranyl group, a phenanthryl group, etc.

The aryl group of (24) "the $C_6$ to $C_{20}$ aryl group having a substituent(s)" has the same meaning as (23) "the $C_6$ to $C_{20}$ aryl group having no substituent".

As the substituent for (24) "the $C_6$ to $C_{20}$ aryl group having a substituent(s)", there may be mentioned, for example, a nitro group; a cyano group; a benzyloxy group; an alkoxycarbonyl group having a straight or branched $C_1$ to $C_6$ alkyl group portion; a trialkylsilyloxy group having the same or different straight or branched $C_1$ to $C_6$ alkyl group portion; a halogen atom; a straight or branched $C_1$ to $C_6$ alkyl group or a straight or branched $C_1$ to $C_6$ alkoxy group.

"The 5- or 6-membered heteroaromatic ring group containing 1 or 2 hetero atoms selected from N, O and S, which may be substituted" represented by $R^4$ in the compound (II) represented by the formula (II) has the same meaning as (25) "a 5- or 6-membered heteroaromatic ring group containing 1 or 2 hetero atoms selected from N, O and S having no substituent" or (26) "a 5- or 6-membered heteroaromatic ring group containing 1 or 2 hetero atoms selected from N, O and S having a substituent(s)".

As the heteroaromatic ring group of (25) "the 5- or 6-membered heteroaromatic ring group containing 1 or 2 hetero atoms selected from N, O and S having no substituent", there may be mentioned, for example, a furyl group, a thienyl group, a pyrrolyl group, a 2H-pyrrolyl group, an oxazolyl group, an isoxazolyl group, a thiazolyl group, an isothiazolyl group, an imidazolyl group, a pyrazolyl group, a pyranyl group, a pyridyl group, a pyridazyl group, a pyrimidyl group or a pyrazinyl group, etc.

As the substituent for (26) "the 5- or 6-membered heteroaromatic ring group containing 1 or 2 hetero atoms selected from N, O and S having a substituent(s)", there may be mentioned, for example, a nitro group; a cyano group; a benzyloxy group; an alkoxycarbonyl group having a straight or branched $C_1$ to $C_6$ alkyl group portion; a trialkylsilyloxy group having the same or different, straight or branched $C_1$ to $C_6$ alkyl group portion; a halogen atom; a straight or branched $C_1$ to $C_6$ alkyl group; or a straight or branched $C_1$ to $C_6$ alkoxy group. Incidentally, the number and the position of the substituent are not limited.

"The $C_1$ to $C_6$ alkoxycarbonyl group which may be substituted" represented by $R^4$ in the compound (II) represented by the formula (II) means (27) "a $C_1$ to $C_6$ alkoxycarbonyl group having no substituent" or (28) "a $C_1$ to $C_6$ alkoxycarbonyl group having a substituent(s)".

As the alkoxycarbonyl group of (27) "the $C_1$ to $C_6$ alkoxycarbonyl group having no substituent", there may be mentioned, for example, a straight or branched $C_1$ to $C_6$ alkoxycarbonyl group such as a methoxycarbonyl group, an ethoxycarbonyl group, a n-propionyloxycarbonyl group, an isopropyloxycarbonyl group, a n-butoxycarbonyl group, a tert-butoxycarbonyl group, a n-pentyloxycarbonyl group, a n-hexyloxycarbonyl group, etc.

As the substituent for (28) "the $C_1$ to $C_6$ alkoxycarbonyl group having a substituent(s)", there may be mentioned, for example, a nitro group; a cyano group; a benzyloxy group; an alkoxycarbonyl group having a straight or branched $C_1$ to $C_6$ alkyl group portion; a trialkylsilyloxy group having the same or different straight or branched $C_1$ to $C_6$ alkyl group portion; a halogen atom; a straight or branched $C_1$ to $C_6$ alkoxy group, etc. Incidentally, the number and the position of the substituent(s) are not limited.

Specific examples of such $R^4$ may include, for example, a hydrogen atom, a methyl group, an ethyl group, a n-propyl group, an isopropyl group, a n-butyl group, an isobutyl group, a sec-butyl group, a tert-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, an n-eicosyl group, a methoxymethyl group, an acetyloxymethyl group, a benzyloxymethyl group, a tert-butyloxymethyl group, a 1-methoxyethyl group, a 1-benzyloxyethyl group, a 1-benzyloxypropyl group, a 1-benzyloxybutyl group, a 1-phenylethyl group, a 2-phenylethyl group, a 3-phenylpropyl group, a phenylmethyl group, a 2-chloroethyl group, a 2-fluoroethyl group, a monofluoromethyl group, a trifluoromethyl group, a BocNH-methyl group (Boc=tert-butoxycarbonyl), a CbzNH-methyl group (Cbz=benzyloxycarbonyl), a benzoyl group, an acetyl group, a methoxycarbonyl group, an ethoxycarbonyl group, a menthyloxycarbonyl group, a methylthiomethyl group, a methoxycarbonylmethyl group, a 3-BocNH-propyl group, a 4-BocNH-butyl group, an acylaminoethyl group, a 2-benzyloxypropyl group, a cyclohexylmethyl group, a 1-methyl-3-methoxycarbonylbutyl group, a 1-cyclohexylethyl group, a 2-(N-Boc-piperidy) methyl group, a vinyl group, a 1-propenyl group, a 2-propenyl group, a 1-butenyl group, a 2-butenyl group, a styryl group, a 4-nitrostyryl group, a 4-chlorostyryl group, a 4-methylstyryl group, a 4-methoxystyryl group, a 3-phenyl-2-propenyl group, a 3-phenyl-1-propenyl group, a 2-hexenyl group, a 2-heptenyl group, a 2-pentenyl group, a 2,4-hexadienyl group, a 1-methyl-3-pentenyl group, a 1-tetradecynyl group, a 1-pentadecynyl group, a 1-hexadecenyl group, a 2,3,12-tribenzyloxy-3-heptadecynyl group, a 2,3,12-tri-tert-butyldimethylsilyloxy-3-heptadecynyl group, a 2-furylvinyl group, a 2-cyclohexylvinyl group, a phenylethyl group, a 3-phenyl-1-propargyl group, a propargyl group, a 1-butynyl group, a 1-pentynyl group, a 1-hexynyl group, a 2-heptynyl group, a 1-octynyl group, a 1-nonenyl group, a cyclopropyl group, a cyclohexyl group, a cyclobutyl group, a cyclopentyl group, a 2-phenylcyclopropyl group, a 2,2-dimethoxycarbonylcyclopropyl group, a phenyl group, a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 4-methylphenyl group, a 4-methoxyphenyl group, a 4-methoxyphenyl group, a 3-methoxyphenyl group, a 4-benzyloxyphenyl group, a 3-benzyloxyphenyl group, a 2-benzyloxyphenyl group, a 3,4-dibenzyloxyphenyl group, a 3,4-methylenedioxyphenyl group, a 3,4-dimethoxyphenyl group, a 4-nitrophenyl group, a 3,5-dibromo-4-benzyloxyphenyl group, a 3,5-dichloro-4-benzyloxyphenyl group, a p-tert-butyldimethylsilyloxyphenyl group, a furyl group, a thienyl group, a thiazolyl group, an isoxazolyl group, an oxazolyl group, a 4-N-methylimidazolyl group, a N-methylindolyl group, etc.

As the compound represented by the formula (II), there may be mentioned aldehydes having the substituent mentioned as $R^4$, more specifically, preferred are benzaldehyde, 4-methoxybenzaldehyde, 2-methoxybenzaldehyde, 3,4-methylenedioxybenzaldehyde, 3,4-dimethoxybenzaldehyde, 4-nitrobenzaldehyde, 2-nitrobenzaldehyde, naphthylaldehyde, acetaldehyde, propionaldehyde, n-butylaldehyde, isobutyl aldehyde, cinnamaldehyde, hydrocinnamaldehyde, crotonaldehyde, phenylacetaldehyde, α-benzyloxypropionaldehyde, methylglycidiate, acrolein, tetradecenal and benzyloxyacetaldehyde; more preferred are benzaldehyde, 3,4-methylenedioxybenzaldehyde, 3,4-dimethoxybenzaldehyde, isobutyl aldehyde, cinnamaldehyde, hydrocinnamaldehyde and methylglycidiate.

As the compound (III), compounds comprising a combination of the substituents described as $R^1$, $R^2$, $R^3$ and $R^4$ as mentioned above may be mentioned. As the specific compound (III) thereof, the following compounds may be mentioned.

There may be mentioned, for example, 3-diphenylmethyl-4-methoxycarbonyl-5-phenyl-2-oxazolidinone, 3-diphenylmethyl-4-methoxycarbonyl-5-(3,4-dimethoxyphenyl)-2-oxazolidinone, 3-diphenylmethyl-4-methoxycarbonyl-5-(4-benzyloxyphenyl)-2-oxazolidinone, 3-diphenylmethyl-4-methoxycarbonyl-5-(3,4-methylenedioxyphenyl)-2-oxazolidinone, 3-diphenylmethyl-4-methoxycarbonyl-5-(3,4-dibenzyloxyphenyl)-2-oxazolidinone, 3-diphenylmethyl-4-methoxycarbonyl-5-(3,4-ditrimethylsilyloxyphenyl)-2-oxazolidinone, 3-diphenylmethyl-4-ethoxycarbonyl-5-phenyl-2-oxazolidinone, 3-diphenylmethyl-4-isopropoxycarbonyl-5-phenyl-2-oxazolidinone, 3-diphenylmethyl-4-tert-butoxycarbonyl-5-phenyl-2-oxazolidinone, 3-diphenylmethyl-4-((1)-menthyloxycarbonyl)-5-phenyl-2-oxazolidinone, 3-diphenylmethyl-4-(8-phenylmenthyloxycarbonyl)-5-phenyl-2-oxazolidinone, 3-diphenylmethyl-4-methoxycarbonyl-5-isopropyl-2-oxazolidinone, 3-diphenylmethyl-4-methoxycarbonyl-5-(2-phenylethyl)-2-oxazolidinone, 3-diphenylmethyl-4-methoxycarbonyl-5-methyl-2-oxazolidinone, 3-diphenylmethyl-4-methoxycarbonyl-5-(3-BocNH-propyl)-2-oxazolidinone, 3-diphenylmethyl-4-methoxycarbonyl-5-(methoxycarbonylmethyl)-2-oxazolidinone, 3-diphenylmethyl-4-methoxycarbonyl-5-tridecyl-2-oxazolidinone, 3-diphenylmethyl-4-methoxycarbonyl-5-(1-methyl-3-pentenyl)-2-oxazolidione, 3-methyl-4-methoxycarbonyl-5-(1-methyl-3-pentenyl)-2-oxazolidinone, 3-diphenylmethyl-4-methoxycarbonyl-5-(1-pentadecenyl)-2-oxazolidinone, 3-diphenylmethyl-4-methoxycarbonyl-5-hydroxymethyl-2-oxazolidinone, 3-diphenylmethyl-4-methoxycarbonyl-5-benzyloxymethyl-2-oxazolidinone, 3-diphenylmethyl-4-methoxycarbonyl-5-acetyloxymethyl-2-oxazolidinone, 3-diphenylmethyl-4-methoxycarbonyl-5-trimethylsilyloxymethyl-2- oxazolidinone, 3-(1-phenylethyl)-4-methoxycarbonyl-5-phenyl-2-oxazolidinone, 3-(1-phenylethyl)-4-methoxycarbonyl-5-(4-benzyloxyphenyl)-2-oxazolidinone, 3-(1-phenylethyl)-4-methoxycarbonyl-5-(3,4-methylenedioxyphenyl)-2-oxazolidinone, 3-(1-phenylethyl)-4-methoxycarbonyl-5-(3,4-dimethoxyphenyl)-2-oxazolidinone, 3-(1-phenylethyl)-4-methoxycarbonyl-5-isopropyl-2-oxazolidinone, 3-(1-phenylethyl)-4-methoxycarbonyl-5-(2-phenylethyl)-2-oxazolidinone, 3-(1-phenylethyl)-4-methoxycarbonyl-5-methyl-2-oxazolidinone, 3-(1-phenylethyl)-4-methoxycarbonyl-5-benzyloxymethyl-2-oxazolidinone, 3-(1-phenylethyl)-4-methoxycarbonyl-5-methoxycarbonylmethyl-2-oxazolidinone, 3-(1-phenylethyl)-4-((l)-menthyloxycarbonyl)-5-phenyl-2-oxazolidinone, 3-(1-phenylethyl)-4-((l)-menthyloxycarbonyl)-5-isopropyl-2-oxazolidinone, 3-(1-phenylethyl)-4-((l)-menthyloxycarbonyl)-5-(2-phenylethyl)-2-oxazolidinone, 3-(1-(1-naphthyl)ethyl)-4-methoxycarbonyl-5-phenyl-2-oxazolidinone, 3-(1-(1-naphthyl)ethyl)-4-methoxycarbonyl-5-phenyl-2-oxazolidinone, 3-(1-(1-naphthyl)ethyl)-4-((l)-menthyloxycarbonyl)-5-phenyl-2-oxazolidinone, 3-(1-(1-naphthyl)ethyl)-4-methoxycarbonyl-5-(3,4-dimethoxyphenyl)-2-oxazolidinone, 3-(1-(1-naphthyl)ethyl)-4-isopropoxycarbonyl-5-(3,4-methylenedioxyphenyl)-2-oxazolidinone, 3-(1-(1-naphthyl)ethyl)-4-isopropoxycarbonyl -5-isopropyl-2-oxazolidinone, 3-((1-(-1-naphthyl)ethyl)-4-isopropoxycarbonyl-5-(2-phenylethyl)-2-oxazolidinone, 3-(1-(-naphthyl)ethyl)-4-isopropoxycarbonyl-5-(2-phenylethynyl)-2-oxazolidinone, 3-(1-(-naphthyl)ethyl)-4-isopropoxycarbonyl-5-methyl-2-oxazolidinone, 3-(1-( 1-naphthyl)ethyl)-4-isopropoxycarbonyl-5-cyclopropyl-2-oxazolidinone, 3-(1-(1-naphthyl)ethyl)-4-methoxycarbonyl-5-cyclohexyl-2-oxazolidinone, 3-(1-(1-naphthyl)ethyl)-4-isopropoxycarbonyl-5-(1-propenyl)-2-oxazolidinone, 3-(1-(1-naphtyl)ethyl-4-methoxycarbonyl-5-(4-benzyloxyphenyl)-2-oxazolidin-one, 3-(1-(1-naphthyl)ethyl)-4-methoxycarbonyl-5-(3,4-methylenedioxyphenyl)-2-oxazolidinone, 3-(1-(1-naphthyl)ethyl)-4-methoxycarbonyl-5-(3,4-dibenzyloxyphenyl)-2-oxazolidinone, 3-(1-(1-naphthyl)ethyl)-4-methoxycarbonyl-5-(3,4-ditrimethylsilyloxyphenyl)-2-oxazolidinone, 3-(1-(1-naphthyl)ethyl)-4-ethoxycarbonyl-5-phenyl-2-oxazolidinone, 3-(1-(1-naphthyl)ethyl)-4-isopropoxycarbonyl-5-phenyl-2-oxazolidinone, 3-(1-(1-naphthyl)ethyl)-4-tert-butoxycarbonyl-5-phenyl-2-oxazolidinone, 3-(1-(1-naphthyl)ethyl)-4-((l)-menthyloxycarbonyl)-5-phenyl-2-oxazolidinone, 3-(1-(1-naphthyl)ethyl)-4-(8-phenylmenthyloxycarbonyl)-5-phenyl-2-oxazolidinone, 3-(1-(1-naphthyl)ethyl)-4-methoxycarbonyl-5-isopropyl-2-oxazolidinone, 3-(1-(1-naphthyl)ethyl)-4-methoxycarbonyl-5-(2-phenylethyl)-2-oxazolidinone, 3-(1-(1-naphthyl)ethyl)-4-methoxycarbonyl-5-methyl-2-oxazolidinone, 3-(1-(1-naphthyl)ethyl)-4-methoxycarbonyl-5-(3-BocNH-propyl)-2-oxazolidinone, 3-(1-(1-naphthyl)ethyl)-4-methoxycarbonyl-5-(methoxycarbonylmethyl)-2-oxazolidinone, 3-(1-(1-naphthyl)ethyl)-4-methoxycarbonyl-5-tridecyl-2-oxazolidinone, 3-(1-(1-naphthyl)ethyl)-4-methoxycarbonyl-5-(1-methyl-3-pentenyl)-2-oxazolidinone, 3-(1-(1-naphthyl)ethyl)-4-methoxycarbonyl-5-(1-pentadecenyl)-2-oxazolidinone, 3-(1-(1-naphthyl)ethyl)-4-methoxycarbonyl-5-hydroxymethyl-2-oxazolidinone, 3-(1-(1-naphthyl)ethyl)-4-methoxycarbonyl-5-benzyloxymetyl-2-oxazolidinone, 3-(1-(1-naphthyl)ethyl)-4-methoxycarbonyl-5-acetyloxymethyl-2-oxazolidinone, 3-(1-(1-naphthyl)ethyl)-4-methoxycarbonyl-5-trimethylsilyloxymethyl-2-oxazolidinone, 3-(1-(1-naphthyl)ethyl)-4,5-dimethoxycarbonyl-2-oxazolidinone, 3-diphenylmethyl-4,5-dimethoxycarbonyl-2-oxazolidinone, 3-(1-phenylethyl)-4,5-dimethoxycarbonyl-2-oxazolidinone, 3-diphenylmethyl-4-(8-phenylmenthyloxycarbonyl)-5-isopropyl-2-oxazolidinone, 3-diphenylmethyl- 4-(8-phenylmenthyloxycarbonyl)-5-(2-phenylethyl)-2-oxazolidinone, 3-benzyl-4-(8-phenylmenthyloxycarbonyl)-5-phenyl-2-oxazolidinone, 3-benzyl-4-(8-phenylmenthyloxy-carbonyl)-5-isopropyl-2-oxazolidinone, 3-benzyl-4-(8-phenyl-menthyloxycarbonyl)-5-(2-phenylethyl)-2-oxazolidinone, 3-phenyl-4-methoxycarbonyl-4-methyl-5-phenyl-2-oxazolidinone, 3-(o-chlorophenyl)-4-methoxycarbonyl-5-isopropyl-2-oxazolidinone, 3-phenyl-4-methoxycarbonyl-4-methyl-5-methyl-2-oxazolidinone, 3-(p-chlorophenyl)-4-methoxycarbonyl-4-ethyl-5-phenyl-2-oxazolidinone, 3-phenyl-4-isopropyloxycarbonyl-4-methyl-5-phenyl-2-oxazolidinone, 3-diphenylmethyl-4-phenoxycarbonyl-4-methyl-5-phenyl-2-oxazolidinone, 3-(1-phenylethyl)-4-phenoxycarbonyl-5-phenyl-2-oxazolidinone, 3-phenyl-4-methoxycarbonyl-5-isopropyl-2-oxazolidinone, etc.

As the Lewis acid catalyst to be used in the present invention, the following organometallic compounds, halides, or trifluoromethane sulfonates of elements from Group 2 (Group IIa) to Group 4 (Group IVa) (provided that carbon is excluded) of the Periodic Table, halides or trifluoromethane sulfonates of a Lanthanoid group metal can be specifically used.

Specifically, there may be mentioned the compound represented by the following formula (IV):

$$R^5{}_nX_mM \qquad (IV)$$

wherein $R^5$ represents a $C_1$ to $C_{10}$ alkyl group or a $C_6$ to $C_{20}$ aryl group; X represents a halogen atom; M represents Al, B, Sn or Ti; m and n each represents a number of 0, 1, 2, 3 or 4; provided that m+n is 2, 3 or 4.

The alkyl group represented by $R^5$ in the compound (IV) represented by the formula (IV) represents a $C_1$ to $C_{10}$ alkyl group, and there may be mentioned, for example, a straight or branched $C_1$ to $C_{10}$ alkyl group such as a methyl group, an ethyl group, a propyl group (including an isomer), a butyl group (including isomers thereof), a pentyl group (including isomers thereof), a hexyl group (including isomers thereof), a heptyl group (including isomers thereof), an octyl group (including isomers thereof), a nonyl group (including isomers thereof) or a decyl group (including isomers thereof), etc., preferably a $C_1$ to $C_6$ alkyl group, more preferably a methyl group, an ethyl group, a propyl group, an isopropyl group, a butyl group, an isobutyl group, a sec-butyl group or a tert-butyl group.

The aryl group represented by $R^5$ in the compound (IV) represented by the formula (IV) has the same meaning as the aryl group as "described in (23) and (24)".

X in the compound (IV) represented by the formula (IV) represents, for example, a halogen atom such as a fluorine atom, a chlorine atom, a bromine atom, an iodine atom, etc. M represents Al, B, Sn or Ti. m and n each represents a number of 0, 1, 2, 3 or 4. However, m+n is 2, 3 or 4.

As the specific compounds of the compound (IV) represented by the formula (IV), there may be mentioned, for example, trialkyl aluminum such as trimethyl aluminum, triethyl aluminum, tripropyl aluminum, triisopropyl aluminum, tri-n-butyl aluminum, triisobutyl aluminum, tri-sec-butyl aluminum, tri-tert-butyl aluminum, tripentyl aluminum, trihexyl aluminum, trioctyl aluminum, tridecyl aluminum, etc.; dialkyl aluminum halide such as dimethyl aluminum chloride, diethyl aluminum chloride, diethyl aluminum bromide, diisobutyl aluminum chloride, etc.; dialkyl aluminum hydride such as diethyl aluminum hydride, diisobutyl aluminum hydride, etc., an alkyl aluminum dihalide such as methyl aluminum dichloride, ethyl aluminum dichloride, isobutyl aluminum dichloride, ethyl aluminum dibromide, etc.; aluminum halides such as aluminum (III) chloride, aluminum (III) bromide, aluminum (III) iodide, aluminum (III) fluoride, etc.; boron trihalides such as boron trifluoride, boron trichloride, boron tribromide, etc.; trihaloboranes such as trifluoroborane, trichloroborane, tribromoborane, etc.; triarylboranes such as triphenylborane, tri(4-fluorophenyl)borane, tris(penta-fluorophenyl)borane, etc.; arylborane dihalides such as phenyl dichloroborane, 4-chlorophenyl dichloroborane, phenyl dibromoborane, etc.; arylborane halides such as dimethylfluoroborane, diphenylfluoroborane, etc.; trialkyl boranes such as triethyl borane, tributyl borane, etc.; tin halides such as tin (IV) chloride, tin (II) chloride, tin (IV) bromide, tin (II) bromide, etc.; tetraalkyl tins such as tetraethyl tin, tetrabutyl tin, tetraisopropyl tin, etc.; tetraaryl tins such as tetraphenyl tin, etc.; alkylaryl tins such as benzyltriphenyl tin, pentafluorophenyltrimethyl tin, etc.; trialkyl tin halides such as trimethyl tin bromide, trimethyl tin chloride, triethyl tin bromide, tributyl tin chloride, tribenzyl tin chloride, etc.; triaryl tin halides such as triphenyl tin chloride, etc.; trialkyl tin hydrides such as tributyl tin hydride, etc.; titanium halides such as titanium (IV) chloride, titanium (IV) bromide, titanium (IV) iodide, titanium (IV) fluoride, etc.

Also, as a Lewis acid, the compound represented by the formula (V):

$$(R^6O)_n X_{m'} M \qquad (V)$$

wherein $R^6$ represents a $C_1$ to $C_{10}$ alkyl group or a $C_6$ to $C_{20}$ aryl group; X represents a halogen atom; M represents Al, B, Sn or Ti; m' and n' each represents a number of 0, 1, 2, 3 or 4; provided that m'+n' is 3 or 4, can be also mentioned.

The $C_1$ to $C_{10}$ alkyl group or the $C_6$ to $C_{20}$ aryl group represented by $R^6$ in the compound (V) represented by the formula (V) have the same meanings as the $C_1$ to $C_{10}$ alkyl group or the $C_6$ to $C_{20}$ aryl group represented by $R^5$, respectively.

X in the compound (V) represented by the formula (V) represents, for example, a halogen atom such as a fluorine atom, a chlorine atom, a bromine atom, an iodine atom, etc. M represents Al, B, Sn or Ti. m' and n' each represents a number of 0, 1, 2, 3 or 4. However, m'+n' is 3 or 4.

As the specific compounds of the compound (IV) represented by the formula (IV), there may be mentioned, for example, alkoxytitanium trihalides such as trichloromethoxy titanium, trichloroethoxy titanium, trichloroisopropoxy titanium, trichloro-n-butoxy titanium, tribromoethoxy titanium, tri-bromoisobutoxy titanium, etc.; dialkoxy titanium dihalides such as dichlorodimethoxy titanium, dichlorodiethoxy titanium, dichlorodi-n-butoxy titanium, dichlorodiisopropoxy titanium, dibromodiethoxy titanium, etc.; trialkoxy titanium halides such as chlorotrimethoxy titanium, chlorotriethoxy titanium, chlorotri-n-butoxy titanium, bromotriethoxy titanium, etc.; titanium (IV) alkoxides such as titanium (IV) methoxide, titanium (IV) ethoxide, titanium (IV) isopropoxide, titanium (IV) isobutoxide, titanium (IV) n-butoxide, etc.; dialkyl aluminum alkoxides such as dimethyl aluminum methoxide, diethyl aluminum ethoxide, diethyl aluminum isopropoxide, dibutyl aluminum butoxide, etc.; dialkyl aluminum aryloxides such as diethyl aluminum phenoxide, diethyl aluminum (4-fluorophenoxide), etc.; aluminum (III) alkoxides such as aluminum (III) methoxide, aluminum (III) isoprodpoxide, aluminum (III) butoxide, etc.; aluminum (III) aryloxides such as aluminum (III) phenoxide, etc.; triaryloxy boranes such as triphenoxy borane, etc.; trialkoxy boranes such as trimethoxy borane, tributoxy borane, etc.; diaryloxyborane dihalides such as chlorodiphenoxy borane, bromodiphenoxy borane, fluorodiphenoxy borane, etc.; diaryloxy borane dihalides such as dichlorophenoxy borane, etc.

Moreover, as the Lewis acid, a compound represented by the formula (VI):

$$R^7 R^8 R^9 SiX' \qquad (VI)$$

Wherein $R^7$, $R^8$ and $R^9$ each independently represents a $C_1$ to $C_{10}$ alkyl group or a $C_6$ to $C_{20}$ aryl group; X' represents a halogen atom or $-OSO_2CF_3$.

The $C_1$ to $C_{10}$ alkyl group or the $C_6$ to $C_{20}$ aryl group represented by $R^7$, $R^8$ and $R^9$ in the compound (VI) represented by the formula (VI) have the same meanings as the $C_1$ to $C_{10}$ alkyl group or the $C_6$ to $C_{20}$ aryl group represented by $R^5$, respectively.

X' represents, for example a halogen atom such as a fluorine atom, a chlorine atom, a bromine atom, an iodine atom, etc., or a $-OSO_2CF_3$ group.

Specific compound represented of the compound (VI) represented by the formula (VI) may include, for example, trialkylsilyl halides such as trimethylsilyl chloride, trimethylsilyl bromide, trimethylsilyl iodide, triethylsilyl chloride, triethylsilyl bromide, triethylsilyl iodide, tert-butyldimethylsilyl chloride, tert-butyldimethylsilyl bromide, tert-butyldimethylsilyl iodide, triisopropylsilyl chloride, triisopropylsilyl bromide, triisopropylsilyl iodide, etc.; trialkylsilyl triflates such as trimethylsilyl triflate, triethylsilyl triflate, tert-butyldimethylsilyl triflate, triisopropylsilyl triflate, etc.; triarylsilyl halides such as triphenylsilyl chloride, triphenylsilyl bromide, triphenylsilyl iodide, etc.; triarylsilyl triflates such as triphenylsilyl triflate, etc.; alkylarylsilyl halides such as tert-butyl-diphenylsilyl chloride, tert-butyldiphenylsilyl bromide, tert-butyldiphenylsilyl iodide, methyldiphenylsilyl chloride, methyldiphenylsilyl bromide, methyldiphenylsilyl iodide, etc.; alkylarylsilyl triflates such as tert-butyldiphenylsilyl triflate, methyldiphenylsilyl triflate, etc.

In addition, there may be mentioned metal halides or triflates such as zirconium (IV) chloride, zinc (II) chloride, zinc (II) bromide, iron (III) chloride, iron (II) chloride, iron (III) bromide, iron (II) bromide, iron (III) iodide, iron (II) iodide, magnesium chloride, magnesiumbromide, tin triflate (II), etc.; halides or triflates of rare earth metals such as lanthanum (III) triflate, lanthanum (III) chloride, praseodymium (III) triflate, neodymium (III) triflate, samarium (III) triflate, samarium (II) iodide, samarium (III) chloride, europium (III) triflate, gadolinium (III) triflate, dysprosium (III) triflate, holmium (III) triflate, erbium (III) triflate, ytterbium (III) triflate, lutetium (III) triflate, scandium (III) triflate, cerium (III) chloride, etc.

The 4-alkoxycarbonyl-2-oxazolidinone compound represented by the compound (III) can be produced according to the method of the reaction formula (1) as mentioned above.

That is, the production of the compound (III) can be accomplished by reacting the 5-alkoxy-2(3H)oxazolone compound represented by the formula (I) with the aldehyde compound represented by the formula (II) in the presence of a Lewis acid catalyst in a solvent.

An amount of the Lewis acid catalyst to be used may be mentioned in a ratio of usually 0.001 to 5.0 equivalents, preferably 0.005 to 0.5 equivalent based on 1 mol of the compound (I).

As the solvent to be used, it is not particularly limited so long as it directly participate the present reaction, and there may be mentioned, for example, aromatic hydrocarbons such as benzene, toluene, xylene, etc., chlorinated hydrocarbons such as chlorobenzene, dichlorobenzene, methylene chloride, chloroform, carbon tetrachloride, 1,2-dichloroethane, etc., esters such as methyl acetate, ethyl acetate, butyl acetate, etc., ethers such as diethyl ether, diisopropyl ether, dibutyl ether, dimethoxyethane, tetrahydrofuran, dioxane, etc., dimethylformamide, dimethylsulfoxide, acetonitrile, propionitrile, water, etc., but preferably toluene, xylene, methylenechloride, 1,2-dichloroethane, acetonitrile, propionitrile are preferably used.

An amount of the solvent can be used in an amount of 100 to 5000 ml, preferably 300 to 3000 ml based on 1 mol of the compound (I).

Synthetic step of the compound (III) is preferably in an inert gas atmosphere such as nitrogen, argon, helium, etc., the reaction temperature is $-100$ to $100°$ C., preferably $-80$ to $40°$ C., and the reaction time can be suitably selected depending on the reaction time, concentrations of the starting materials to be charged, kinds of the starting materials to be charged, etc., but generally 1 to 10 hours. An amount of the starting material is that the compound (II) is used in an amount of 0.8 to 3-fold moles, preferably 0.9 to 1.2-fold moles based on the compound (I).

As a method of obtaining a reaction mixture containing the formed compound (III) in the present invention, usual washing operation and separating operation are carried out in combination. For example, a formed salt is removed by filtration operation, the filtrate is subjected to removal operation such as washing with water, dehydration by a drier and concentration of an organic solvent whereby a crude product of the compound (III) can be obtained. When the compound is to be further purified, purification can be carried out by the conventionally known means such as column chromatography, recrystallization, etc.

Also, the compound (III) of the present invention can be obtained by applying the specific preparation method described in Examples.

Incidentally, in the resulting compound (III), β-hydroxy-α-amino acid can be easily derived by subjecting to hydrolysis at the ester portion or carbamate portion, as reported in, for example, J. Am. Chem. Soc., 1996, 118, 3584–3590 and it would be clear. Moreover, when $R^1$ is a diphenylmethyl group, a benzyl group, a 1-phenylethyl group, a 1-(1-naphthyl)ethyl group, deprotection is possible by hydrogenation reaction using a Pd catalyst to give a free amino group which is also described in the above-mentioned reference and would be clear.

EXAMPLES

In the following, the present invention is specifically explained by referring to Examples. Incidentally, the scope of the present invention is not limited by these Examples.

Example 1

Synthesis of 3-diphenylmethyl-4-methoxycarbonyl-5-phenyl-2-oxazolidinone

In 4 ml of methylene chloride were dissolved 0.281 g (1.0 mmol) of 3-diphenylmethyl-5-methoxy-2(3H)oxazolone and 0.106 g (1.0 mmol) of benzaldehyde, and the mixture was cooled to $-78°$ C. under argon atmosphere, and 14 mg (0.1 mmol) of $BF_3 \cdot Et_2O$ was added to the mixture and the resulting mixture was reacted at $-78°$ C. for 3 hours under stirring.

Moreover, the temperature was raised to $-20°$ C. and 15 ml of an aqueous saturated sodium hydrogen carbonate solution was added to the resulting reaction mixture, and the resulting mixture was extracted with 10 ml of methylene chloride. The organic layer was washed with a saturated saline solution and dried over anhydrous magnesium sulfate, and concentrated under reduced pressure to obtain 3-diphenylmethyl-4-methoxycarbonyl-5-phenyl-oxazolidinone as white crystal (0.4 g). According to the HPLC analysis, a formation ratio of cis/trans isomers of the formed product was 2/98. Yield based on 3-diphenylmethyl-5-methoxy-2(3H)oxazolone was substantially quantitative.

Melting point: 99 to 102° C.

IR (KBr, cm$^{-1}$): 1760 (s).

$^1$H-NMR (δ, CDCl$_3$) (trans-isomer): 3.40 (s, 3H), 4.21 (d, J=3.9 Hz, 1H), 5.44 (d, J=3.9 Hz, 1H), 6.27 (s, 1H), 7.0–7.45 (m, 15H).

MS (CI, i-C$_4$H$_{10}$) m/z: 388 (MH$^+$)

Example 2

Synthesis of 3-diphenylmethyl-4-methoxycarbonyl-5-phenyl-2-oxazolidinone

Under argon atmosphere, 141 mg (0.5 mmol) of 3-diphenylmethyl-5-methoxy-2(3H)oxazolone was dissolved in 3 ml of methylene chloride, and after cooling the mixture to $-78°$ C., 53.1 mg (0.5 mmol) of benzaldehyde and 0.05 ml (0.05 mmol) of a methylene chloride solution containing 1.0 M-t-butyldimethylsilyl triflate were added to the mixture and reacted under stirring for one hour.

Moreover, after elevating the temperature to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure to obtain 174 mg (0.448 mmol) of 3-diphenylmethyl-4-methoxycarbonyl-5-phenyl-2-oxzolidinone as white crystal. (Yield based on 3-diphenylmethyl-5-methoxy-2(3H)oxazolone: 90%.) According to HPLC analysis, a formation ratio of cis/trans-isomers of the formed product was 6/94.

Example 3

Synthesis of 3-diphenylmethyl-4-methoxycarbonyl-5-phenyl-2-oxazolidinone

Under argon atmosphere, in 3 ml of methylene chloride was dissolved 141 mg (0.5 mmol) of 3-diphenylmethyl-5-methoxy-2(3H)oxazolone, and after cooling the solution to $-78°$ C., 53.1 mg (0.5 mmol) of benzaldehyde and 0.05 ml (0.05 mmol) of a methylene chloride solution containing 1.0 M-SnCl$_4$ were added to the solution and the mixture was reacted under stirring for 2 hours.

Moreover, the temperature of the mixture was raised to room temperature (20° C.), and after stirring for further 15 hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrated residue was quantitated by the HPLC method, yield of 3-diphenylmethyl-4-methoxycarbonyl-5-phenyl-2- oxzolidinone was 43%. In this case, a formation ratio of cis/trans-isomers of the formed product was 7/93.

Example 4

Synthesis of 3-diphenylmethyl-4-methoxycarbonyl-5-phenyl-2-oxazolidinone

Under argon atmosphere, in 3 ml of methylene chloride was dissolved 141 mg (0.5 mmol) of 3-diphenylmethyl-5-methoxy-2(3H)oxazolone, and after cooling the solution to −78° C., 53.1 mg (0.5 mmol) of benzaldehyde and 0.05 ml (0.05 mmol) of a methylene chloride solution containing 1.0 M-TiBr$_4$ were added to the solution and the mixture was reacted under stirring for 2 hours. Then, the temperature of the mixture was raised to room temperature, and after stirring for further 16 hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrated residue was quantitated by the HPLC method, yield of 3-diphenylmethyl-4-methoxycarbonyl-5-phenyl-2-oxzolidinone was 26%. A formation ratio of cis/trans-isomers of the formed product was 8/92.

Example 5

Synthesis of 3-diphenylmethyl-4-methoxycarbonyl-5-phenyl-2-oxazolidinone

Under argon atmosphere, in 3 ml of methylene chloride was dissolved 141 mg (0.5 mmol) of 3-diphenylmethyl-5-methoxy-2(3H)oxazolone, and after cooling the solution to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour. After the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure to obtain 184 mg (0.476 mmol) of 3-diphenylmethyl-4-methoxycarbonyl-5-phenyl-2-oxzolidinone as white crystal. (Yield based on 3-diphenylmethyl-5-methoxy-2(3H)oxazolone: 95%.) According to HPLC analysis, a formation ratio of cis/trans-isomers of the formed product was 5/95.

Example 6

Synthesis of 3-diphenylmethyl-4-methoxycarbonyl-5-isopropyl-2-oxazolidinone

In 3 ml of methylene chloride were dissolved 0.281 g (1.0 mmol) of 3-diphenylmethyl-5-methoxy-2(3H)oxazolone and 0.072 g (1.0 mmol) of isobutyl aldehyde, and after cooling the solution to −78° C. under argon atmosphere, 14 mg (0.1 mmol) of BF$_3$.Et$_2$O was added to the solution and the mixture was reacted under stirring at −78° C. for 2 hours.

Moreover, the temperature of the mixture was raised to around 0° C., and 15 ml of a saturated aqueous sodium hydrogen carbonate solution was added to the resulting reaction mixture and the mixture was extracted with 10 ml of methylene chloride. The organic layer was washed with a saturated salt solution, dried over anhydrous magnesium sulfate and concentrated under reduced pressure to obtain 3-diphenylmethyl-4-methoxycarbonyl-5-iso-propyl-2-oxzolidinone as colorless transparent oily substance (0.35 g). According to the HPLC analysis, a formation ratio of cis/trans isomers of the formed product was 15/85. Yield based on 3-diphenylmethyl-5-methoxy-2(3H)oxazolone was substantially quantitative.

cis-trans mixture

IR (neat, cm$^{-1}$): 1762 (s), 1400 (m).

$^1$H-NMR (δ, CDCl$_3$) (trans-isomer): 0.90 (d, J=6.8 Hz, 3H), 0.96 (d, J=6.4 Hz, 3H), 1.90 (m, 1H), 3.38 (s, 3H), 3.96 (d, J=4.9 Hz, 1H), 4.14 (dd, J=6.8 Hz, 4.9 Hz, 1H), 6.19 (s, 1H), 7.2–7.4 (m, 10H).

MS (EI) m/z: 353 (MH$^+$), 167.

Example 7

Synthesis of 3-diphenylmethyl-4-methoxycarbonyl-5-(2-phenylethyl)-2-oxazolidinone In 3 ml of methylene chloride were dissolved 0.281 g (1.0 mmol) of 3-diphenylmethyl-5-methoxy-2(3H)oxazolone and 0.134 g (1.0 mmol) of hydrocinnamaldehyde, and after cooling the solution to −78° C. under argon atmosphere, 14 mg (0.1 mmol) of BF$_3$.Et$_2$O was added to the solution and the mixture was reacted under stirring at −78° C. for 2 hours.

Moreover, the temperature of the mixture was raised to around −20° C., and 15 ml of a saturated aqueous sodium hydrogen carbonate solution was added to the resulting reaction mixture and the mixture was extracted with 10 ml of methylene chloride. The organic layer was washed with a saturated salt solution, dried over anhydrous magnesium sulfate and concentrated under reduced pressure. By adding n-hexane to the residue, the material was crystallized to obtain 3-diphenylmethyl-4-methoxycarbonyl-5-(2-phenylethyl)-2-oxzolidinone as white crystal (0.41 g). According to the HPLC analysis, a formation ratio of cis/trans isomers of the formed product was 5/95. Yield based on 3-diphenylmethyl-5-methoxy-2(3H)oxazolone was 99%.

cis-trans mixture

Melting point: 104 to 106° C.

IR (KBr, cm$^{-1}$): 1762 (s), 1399 (m).

$^1$H-NMR (δ, CDCl$_3$) (trans-isomer): 2.05 (m, 2H), 2.75 (m, 2H), 3.35 (s, 3H), 3.93 (d, J=4.4 Hz, 1H), 4.36 (m, 1H), 6.21 (s, 1H), 7.15–7.37 (m, 15H).

MS (EI) m/z: 415 (M$^+$), 167.

Example 8

Synthesis of 3-(1-phenylethyl)-4-methoxycarbonyl-5-phenyl-2-oxazolidinone

In 4 ml of methylene chloride were dissolved 0.22 g (1.0 mmol) of 3-(1-phenylethyl)-5-methoxy-2(3H)oxazolone and 0.106 g (1.0 mmol) of benzaldehyde, and after cooling the solution to −78° C. under argon atmosphere, 14 mg (0.1 mmol) of BF$_3$.Et$_2$O was added to the solution and the mixture was reacted under stirring at −78° C. for 2 hours.

Moreover, the temperature of the mixture was raised to around 0° C., and 15 ml of a saturated aqueous sodium hydrogen carbonate solution was added to the resulting reaction mixture and the mixture was extracted with 10 ml of methylene chloride. The organic layer was washed with a saturated salt solution, dried over anhydrous magnesium sulfate and concentrated under reduced pressure to obtain 3-(1-phenylethyl)-4-methoxycarbonyl-5-phenyl-2-oxazolidinone as colorless transparent oily substance (0.32 g). By adding n-hexane to the residue, the material was obtained as a white crystal. According to $^1$H-NMR, a formation ratio of cis/trans isomers of the formed product was 1/99 and a diastereomer ratio of the trans-isomer was 70/30. Yield based on 3-(1-phenylethyl)-5-methoxy-2(3H) oxazolone was 98%.

trans isomer (diastereomer mixture)
Melting point: 98 to 106° C.
IR (KBr, cm$^{-1}$) : 1737 (s), 1399 (m).
$^1$H-NMR (δ, CDCl$_3$) (trans-isomer, major isomer): 1.58 (d, J=6.8 Hz, 3H), 3.82 (s, 3H), 3.84 (d, J=4.4 Hz, 1H), 5.32 (d, J=4.4 Hz, 1H), 5.30 (q, J=6.8 Hz, 1H), 7.07–7.40 (m, 10H), (trans-isomer, minor isomer): 1.62 (d, J=6.8 Hz, 3H), 3.32 (s, 3H), 4.13 (d, J=4.4 Hz, 1H), 5.20 (q, J=6.8 Hz, 1H), 5.36 (d, J=4.4 Hz, 1H), 7.07–7.40 (m, 10H).
MS (CI, i-C$_4$H$_{10}$) m/z: 326 (MH$^+$), 105.

Example 9

Synthesis of 3-((R)-1-phenylethyl)-4-methoxycarbonyl-5-phenyl-2-oxazolidinone

Under argon atmosphere, in 3 ml of methylene chloride was dissolved 110 mg (0.5 mmol) of 3-((R)-1-phenylethyl)-5-methoxy-2(3H)oxazolone, and after cooling the solution to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the obtained concentrated residue was quantitated by the HPLC method, yield of 3-((R)-1-phenylethyl)-4-methoxycarbonyl-5-phenyl-2-oxazolidinone was 95%. A formation ratio of cis/trans isomers of the formed product was 1/99 according to the $^1$H-NMR analysis and a diastereomer ratio of the trans-isomer was 72/28.

Example 10

Synthesis of 3-((R)-1-phenylethyl)-4-methoxycarbonyl-5-phenyl-2-oxazolidinone

Under argon atmosphere, in 3 ml of methylene chloride was dissolved 110 mg (0.5 mmol) of 3-((R)-1-phenylethyl)-5-methoxy-2(3H)oxazolone, and after cooling the solution to −78° C., 53.1 mg (0.5 mmol) of benzaldehyde and 0.05 ml (0.05 mmol) of a methylene chloride solution containing 1.0 M-t-butyldimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrate was quantitated by the HPLC method, yield of 3-((R)-1-phenylethyl)-4-methoxycarbonyl-5-phenyl-2-oxazolidinone was 85%. A formation ratio of cis/trans isomers of the formed product was 5/95 according to the $^1$H-NMR analysis and a diastereomer ratio of the trans-isomer was 70/30.

Example 11

Synthesis of 3-((R)-1-phenylethyl)-4-methoxycarbonyl-5-phenyl-2-oxazolidinone

Under argon atmosphere, in 3 ml of methylene chloride was dissolved 110 mg (0.5 mmol) of 3-((R)-1-phenylethyl)-5-methoxy-2(3H)oxazolone, and after cooling the solution to −78° C., 53.1 mg (0.5 mmol) of benzaldehyde and 0.1 ml (0.1 mmol) of a methylene chloride solution containing 1.0 M-SnCl$_4$ were added to the solution and the mixture was reacted under stirring for one hour.

Moreover, after the temperature of the mixture was raised up to the room temperature and stirring for further two hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrate was quantitated by the HPLC method, yield of 3-((R)-1-phenylethyl)-4-methoxycarbonyl-5-phenyl-2-oxazolidinone was 78%. A formation ratio of cis/trans isomers of the formed product was 4/96 and a diastereomer ratio of the trans-isomer was 83/17.

Example 12

Synthesis of 3-((R)-1-phenylethyl)-4-methoxycarbonyl-5-phenyl-2-oxazolidinone

Under argon atmosphere, in 3 ml of methylene chloride was dissolved 110 mg (0.5 mmol) of 3 ((R)-1-phenylethyl)-5-methoxy-2(3H)oxazolone, and after cooling the solution to −78° C., 53.1 mg (0.5 mmol) of benzaldehyde and 0.05 ml (0.05 mmol) of a methylene chloride solution containing 1.0 M-BBr$_3$ were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrate was quantitated by the HPLC method, yield of 3-((R)-1-phenylethyl)-4-methoxycarbonyl-5-phenyl-2-oxazolidinone was 86%. A formation ratio of cis/trans isomers of the formed product was 3/97 and a diastereomer ratio of the trans-isomer was 1/1.

Example 13

Synthesis of 3-((R)-1-phenylethyl)-4-methoxycarbonyl-5-phenyl-2-oxazolidinone

Under argon atmosphere, in 3 ml of methylene chloride was dissolved 110 mg (0.5 mmol) of 3-((R)-1-phenylethyl)-5-methoxy-2(3H)oxazolone, and after cooling the solution to −78° C., 53.1 mg (0.5 mmol) of benzaldehyde and 15 mg (0.05 mmol) of trifluoromethanesulfonic acid were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrate was quantitated by the HPLC method, yield of 3-((R)-1-phenylethyl)-4-methoxycarbonyl-5-phenyl-2-oxazolidinone was 67%. A formation ratio of cis/trans isomers of the formed product was 4/96 and a diastereomer ratio of the trans-isomer was 67/33.

Example 14

Synthesis of 3-((S)-1-phenylethyl)-4-iso-propoxycarbonyl-5-phenyl-2-oxazolidinone Under argon atmosphere, in 3 ml of methylene chloride was dissolved 124 mg (0.5 mmol) of 3-((S)-1-phenylethyl)-5-iso-propoxy-2(3H)oxazolone, and after cooling the solution to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure to obtain 3-((S)-1-phenylethyl)-4-isopropoxycarbonyl-5-phenyl-2-oxazolidinone (171 mg (0.485 mmol)) as a brownish oily substance. A formation ratio of cis/trans isomers of the formed product was 1/99 according to $^1$H-NMR and a diastereomer ratio of the trans-isomer was 75/25. Yield based on 3-((S)-1-phenylethyl)-5-isopropoxy2(3H)oxazolone was 97%.

trans isomer (diastereomer mixture)

MS (CI, i-$C_4H_{10}$) m/z: 354 (MH$^+$).

$^1$H-NMR (δ, $CDCl_3$) (trans-isomer, major isomer): 1.30 (d, J=6.3 Hz, 6H), 1.60 (d, J=7.3 Hz, 3H), 3.77 (d, J=4.4 Hz, 1H), 5.14 (m, 1H), 5.28 (d, J=4.4 Hz, 1H), 5.30 (q, J=7.3 Hz, 1H), 7.24–7.39 (m, 10H), (trans-isomer, minor isomer): 1.08 (d, J=6.4 Hz, 6H), 1.65 (d, J=6.8 Hz, 3H), 4.08 (d, J=4.4 Hz, 1H), 4.70 (m, 1H), 5.06 (q, J=6.8 Hz, 1H), 5.31 (d, J=4.4 Hz, 1H), 7.24–7.39 (m, 10H).

Example 15

Synthesis of 3-((S)-1-phenylethyl)-4-iso-propoxycarbonyl-5-phenyl-2-oxazolidinone Under argon atmosphere, in 3 ml of methylene chloride was dissolved 124 mg (0.5 mmol) of 3-((S)-1-phenylethyl)-5-iso-propoxy-2(3H)oxazolone, and after cooling the solution to −78° C., 53.1 mg (0.5 mmol) of benzaldehyde and 0.05 ml (0.05 mmol) of a methylene chloride solution containing 1.0 M-$BF_3.Et_2O$ were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrated residue was quantitated by the HPLC method, yield of 3-((S)-1-phenylethyl)-4-isopropoxycarbonyl-5-phenyl-2-oxazolidinone was 82%. According to $^1$H-NMR, a formation ratio of cis/trans isomers of the formed product was 4/96 and a diastereomer ratio of the trans-isomer was 69/31.

Example 16

Synthesis of 3-((S)-1-phenylethyl)-4-iso-propoxycarbonyl-5-phenyl-2-oxazolidinone Under argon atmosphere, in 3 ml of methylene chloride was dissolved 124 mg (0.5 mmol) of 3-((S)-1-phenylethyl)-5-iso-propoxy-2(3H)oxazolone, and after cooling the solution to −78° C., 53.1 mg (0.5 mmol) of benzaldehyde and 0.05 ml (0.05 mmol) of a methylene chloride solution containing 1.0 M-$TiCl_4$ were added to the solution and the mixture was reacted under stirring for 2. hours.

Moreover, after the temperature of the mixture was raised up to the room temperature and stirring for further one hour, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over an hydrous magnesium sulfate and concentrated under reduced pressure. When the resulting concentrated residue was quantitated by the HPLC method, yield of 3-((S)-1-phenylethyl)-4-isopropoxycarbonyl-5-phenyl-2-oxazolidinone was 59%. According to $^1$H-NMR analysis, no formation of a cis isomer was admitted and a diastereomer ratio of the trans-isomer was 50/50.

Example 17

Synthesis of 3-((S)-1-phenylethyl)-4-iso-propoxycarbonyl-5-phenyl-2-oxazolidinone Under argon atmosphere, in 3 ml of methylene chloride was dissolved 124 mg (0.5 mmol) of 3((S)-1-phenylethyl)-5-iso-propoxy-2(3H)oxazolone, and after cooling the solution to −78° C., 53.1 mg (0.5 mmol) of benzaldehyde and 0.05 ml (0.05 mmol) of a methylene chloride solution containing 1.0 M-$AlCl_3$ were added to the solution and the mixture was reacted under stirring for one hour.

After the temperature of the mixture was raised up to the room temperature and stirring for further one hour, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the resulting concentrated residue was quantitated by the HPLC method, yield of 3-((S)-1-phenylethyl)-4-isopropoxycarbonyl-5-phenyl-2-oxazolidinone was 68%. According to $^1$H-NMR analysis, a formation ratio of cis/trans isomers of the formed product was 5/95 and a diastereomer ratio of the trans-isomer was 66/34.

Example 18

Synthesis of 3-(1-phenylethyl)-4-methoxycarbonyl-5-isopropyl-2-oxazolidinone In 6 ml of methylene chloride were dissolved 0.438 g (2.0 mmol) of 3-(1-phenylethyl)-5-methoxy-2(3H)oxazolone and 0.151 g (2.1 mmol) of isobutyl aldehyde, and the solution was cooled to −78° C. under argon atmosphere, 14 mg (0.1 mmol) of $BF_3.Et_2O$ was added to the solution and the mixture was reacted under stirring at −78° C. for 30 minutes. Thereafter, the temperature was raised up to −40° C. and the mixture was reacted under stirring for one hour.

Moreover, the temperature of the mixture was raised up to around −20° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 3-(1-phenylethyl)-4-methoxycarbonyl-5-isopropyl-2-oxazolidinone as a yellowish transparent oily substance (0.57 g). According to $^1$H-NMR analysis, a formation ratio of cis/trans isomers of the formed product was 7/93 and a diastereomer ratio of the trans-isomer was 80/20. Yield based on 3-(1-phenylethyl)-5-methoxy-2(3H)oxazolone was 96%.

trans isomer (diastereomer mixture)

IR (neat, cm$^{-1}$) 1760 (s), 1406 (m).

$^1$H-NMR (δ, CDCl$_3$) (trans-isomer, major isomer): 0.73 (d, J=6.8 Hz, 3H), 0.76 (d, J=6.8 Hz, 3H), 1.55 (d, J=7.3 Hz, 3H), 1.67 (m, 1H), 3.60 (d, J=4.4 Hz, 1H), 3.78 (s, 3H), 4.80 (dd, J=4.4 Hz, J=5.9 Hz, 1H), 5.27 (q, J=7.3 Hz, 1H), 7.2–7.4 (m, 5H), (trans-isomer, minor isomer): 0.94 (d, J=6.8 Hz, 3H), 0.97 (d, J=6.8 Hz, 3H), 1.67 (d, J=7.3 Hz, 3H), 1.88 (m, 1H), 3.24 (s, 3H), 3.98 (d, J=4.4 Hz, 1H), 4.11 (dd, J=4.4 Hz, J=5.9 Hz, 1H), 5.14 (q, J=7.3 Hz, 1H).

MS (EI) m/z: 291 (M$^+$), 105.

Example 19

Synthesis of 3-(1-phenylethyl)-4-methoxycarbonyl-5-(2-phenylethyl)-2-oxazolidinone In 4 ml of methylene chloride were dissolved 0.22 g (1.0 mmol) of 3-(1-phenylethyl)-5-methoxy-2(3H)oxazolone and 0.134 g (1.0 mmol) of hydrocinnamaldehyde, and the solution was cooled to −78° C. under argon atmosphere, 14 mg (0.1 mmol) of $BF_3.Et_2O$ was added to the solution and the mixture was reacted under stirring at −78° C. for 30 minutes. Thereafter, the temperature was raised up to −40° C. and the mixture was reacted under stirring for one hour.

Moreover, the temperature of the mixture was raised up to around −20° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure, and the residue was applied to silica gel column chromatography (eluent: n-hexane/ethyl acetate=5/1) to obtain 3-(1-phenylethyl)-4-methoxycarbonyl-5-(2-phenylethyl)-2-oxazolidinone as a yellowish transparent oily substance (0.30 g). A formation ratio of cis/trans isomers of the formed product was 7/93, and according to $^1$H-NMR analysis, a diastereomer ratio of the trans-isomer was 86/14. Yield based on 3-(1-phenylethyl)-5-methoxy-2(3H)oxazolone was 84%. transisomer (diastereomer mixture)

IR (neat, cm$^{-1}$): 1760 (s), 1404 (m).

$^1$H-NMR (δ, CDCl$_3$) (trans-isomer, major isomer): 1.56 (d, J=7.3 Hz, 3H), 1.76 (m, 2H), 2.58 (t, J=7.8 Hz, 2H), 3.55 (d, J=3.9 Hz, 1H), 4.30 (m, 1H), 5.28 (q, J=7.8 Hz, 1H), 7.1–7.4 (m, 10H).

MS (EI) m/z: 353 (M$^+$), 105.

Example 20

Synthesis of 3-((R)-1-(1-naphthyl)ethyl)-4-methoxycarbonyl-5-phenyl-2-oxazolidinone In 4 ml of methylene chloride were dissolved 0.27 g (1.0 mmol) of 3-((R)-1-(1-naphthyl)ethyl)-5-methoxy-2(3H) oxazolone and 0.106 g (1.0 mmol) of benzaldehyde, and the solution was cooled to −78° C. under argon atmosphere, 14 mg (0.1 mmol) of $BF_3.Et_2O$ was added to the solution and the mixture was reacted under stirring for 2 hours.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 3-((R)-1-(1-naphthyl)ethyl)-4-methoxycarbonyl-5-phenyl-2-oxazolidinone as a colorless transparent oily substance (0.37 g). According to $^1$H-NMR analysis, no formation of a cis isomer was admitted and a diastereomer ratio of the trans-isomer was 72/28. Yield based on 3-((R)-1-(1-naphthyl)ethyl)-5-methoxy-2(3H)oxazolone was 99%.

trans isomer (diastereomer mixture)

IR (neat, cm$^{-1}$): 1752 (s), 1402 (m).

$^1$H-NMR (δ, CDCl$_3$) (trans-isomer, major isomer): 1.83 (d, J=6.8 Hz, 3H), 3.30 (d, J=4.9 Hz, 1H), 3.73 (s, 3H), 5.19 (d, J=4.9 Hz, 1H), 6.00 (q, J=6.8 Hz, 1H), 6.8–7.9 (m, 12H), (trans-isomer, minor isomer): 1.67 (d, J=6.8 Hz, 3H), 2.61 (s, 3H), 4.11 (d, J=4.4 Hz, 1H), 5.20 (d, J=4.4 Hz, 1H), 6.09 (q, J=6.8 Hz, 1H).

MS (EI) m/z: 375 (M$^+$), 155, 106.

Example 21

Synthesis of 3-((R)-1-(1-naphthyl)ethyl)-4-methoxycarbonyl-5-phenyl-2-oxazolidinone Under argon atmosphere, in 3 ml of methylene chloride was dissolved 135 mg (0.5 mmol) of 3-((R)-1-(1-naphthyl) ethyl)-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. When the obtained concentrated residue was quantitated by the HPLC method, yield of 3-((R)-1-(1-naphthyl) ethyl)-4-methoxycarbonyl-5-phenyl-2-oxazolidinone was 92%. A formation ratio of cis/trans isomers of the formed product was 1/99, and a diastereomer ratio of the trans-isomer was 86/14.

Example 22

Synthesis of 3-((R)-1-(1-naphthyl)ethyl)-4-methoxycarbonyl-5-phenyl-2-oxazolidinone Under argon atmosphere, in 3 ml of methylene chloride was dissolved 135 mg (0.5 mmol) of 3-((R)-1-(1-naphthyl)

ethyl)-5-methoxy-2(3H)oxazolone, and after the solution was cooled to −78° C., 53.1 mg (0.5 mmol) of benzaldehyde and 0.1 ml (0.1 mmol) of a methylene chloride solution containing 1.0 M-SnCl$_4$ were added to the solution and the mixture was raised to the room temperature and reacted under stirring for 20 hours.

To the resulting reaction mixture was added 15 ml of a saturated aqueous sodium hydrogen carbonate solution and the mixture was extracted with 20 ml of methylene chloride. The organic layer was washed with a saturated aqueous sodium chloride solution, dried over anhydrous magnesium sulfate and concentrated under reduced pressure. When the obtained concentrated residue was quantitated by the HPLC method, yield of 3-((R)-1-(1-naphthyl)ethyl)-4-methoxycarbonyl-5-phenyl-2-oxazolidinone was 54%. A formation ratio of cis/trans isomers of the formed product was 5/95, and a diastereomer ratio of the trans-isomer was 81/19.

Example 23

Synthesis of 3-((R)-1-(1-naphthyl)ethyl)-4-methoxycarbonyl-5-(2-phenylethyl)-2-oxazolidinone In 4 ml of methylene chloride were dissolved 0.27 g (1.0 mmol) of 3-((R)-1-(1-naphthyl)ethyl)-5-methoxy-2(3H) oxazolone and 0.134 g (1.0 mmol) of hydrocinnamaldehyde, and under argon atmosphere, the solution was cooled to −78° C., and 14 mg (0.1 mmol) of BF$_3$.Et$_2$O was added to the solution and the mixture was reacted under stirring at −78° C. for 2 hours.

Moreover, the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. By adding n-hexane to the residue, the material was crystallized to obtain 3-((R)-1-(1-naphthyl)ethyl)-4-methoxycarbonyl-5-(2-phenylethyl)-2-oxazolidinone as white crystal (0.36 g). According to $^1$H-NMR analysis, a formation ratio of the cis/trans isomers of the formed product was 1/99 and a diastereomer ratio of the trans-isomer was 97/3. Yield based on 3-((R)-1-(1-naphthyl) ethyl)-5-methoxy-2(3H)oxazolone was 99%.

trans isomer (diastereomer mixture)

Melting point: 145 to 147° C.

IR (neat, cm$^{-1}$): 1745 (s), 1414 (m).

$^1$H-NMR (δ, CDCl$_3$) (trans-isomer, major isomer): 1.45 (m, 2H), 1.79 (d, J=6.8 Hz, 3H), 2.38 (t, J=7.8 Hz, 2H), 2.99 (d, J=3.9 Hz, 1H), 3.69 (s, 3H), 4.19 (m, 1H), 5.94 (q, J=6.8 Hz, 1H), 6.8–7.9 (m, 12H).

MS (EI) m/z: 403 (M$^+$), 155.

Example 24

Synthesis of 3-((R)-1-(1-naphthyl)ethyl)-4-methoxycarbonyl-5-isopropyl-2-oxazolidinone In 3 ml of methylene chloride were dissolved 0.141 g (0.52 mmol) of 3-((R)-1-(1-naphthyl)ethyl)-5-methoxy-2 (3H)oxazolone and 0.04 g (0.55 mmol) of isobutyl aldehyde, and under argon atmosphere, the solution was cooled to −78° C., and 10 mg of BF$_3$.Et$_2$O was added to the solution and the mixture was reacted under stirring at −78° C. for 2 hours.

Moreover, the temperature of the mixture was raised up to −20° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. By adding n-hexane to the residue, the material was crystallized to obtain 3-((R)-1-(1-naphthyl)ethyl)-4-methoxycarbonyl-5-isopropyl-2-oxazolidinone as white crystal (0.17 g). According to $^1$H-NMR, a formation ratio of the cis/trans isomers of the formed product was 1/99 and a diastereomer ratio of the trans-isomer was 93/7. Moreover, by washing the crystal with n-hexane, 0.12 g of a main isomer of the trans-isomer could be obtained with a purity of 99%. Yield based on 3-((R)-1-(1-naphthyl)ethyl)-5-methoxy-2(3H)oxazolone was 96%.

trans isomer (major isomer)

Melting point: 102 to 106° C.

IR (neat, cm$^{-1}$): 1751 (s), 1732 (s), 1413 (m).

$^1$H-NMR (δ, CDCl$_3$): 1.45 (m, 2H), 1.79 (d, J=6.8Hz, 3H), 2.38 (t, J=7.8 Hz, 2H), 2.99 (d, J=3.9 Hz, 1H), 3.69 (s, 3H), 4.19 (m, 1H), 5.94 (q, J=6.8 Hz, 1H), 6.8–7.9 (m, 12H).

MS (EI) m/z: 341 (M$^+$), 155.

Example 25

Synthesis of 3-diphenylmethyl-4-methoxycarbonyl-5-tridecyl-2-oxazolidinone

In 4 ml of methylene chloride were dissolved 0.438 g (2.0 mmol) of 3-diphenylmethyl-5-methoxy-2(3H)oxazolone and 0.424 g (2.0 mmol) of tetradecyl aldehyde, and under argon atmosphere, the solution was cooled to −20° C., and 28 mg (0.2 mmol) of BF$_3$.Et$_2$O was added to the solution and the mixture was reacted under stirring at the state for 2 hours and further at 0° C. for one hour.

To the resulting reaction mixture was added 15 ml of a saturated aqueous sodium hydrogen carbonate solution and the mixture was extracted with 20 ml of methylene chloride. The organic layer was washed with a saturated aqueous sodium chloride solution, dried over anhydrous magnesium sulfate and concentrated under reduced pressure. By adding 5 ml of methanol to the obtained residue, the material was crystallized to obtain 0.6 g of 3-diphenylmethyl-4-methoxycarbonyl-5-tridecyl-2-oxazolidinone as white crystal. According to HPLC analysis, a formation ratio of the cis/trans isomers of the formed product was 10/90. Yield based on 3-diphenylmethyl-5-methoxy-2(3H)oxazolone was 70%.

cis-trans isomers (mixture)

Melting point: 61 to 65° C.

IR (KBr, cm$^{-1}$): 1772 (s), 1740 (s), 1393 (m).

$^1$H-NMR (δ, CDCl$_3$) (trans isomer): 0.88 (t, J=6.6 Hz, 3H), 1.1–1.7 (m, 24H), 3.37 (s, 3H), 3.92 (d, J=4.4 Hz), 1H, 4.33 (m, 1H), 6.20 (s, 1H), 7.2–7.4 (m, 10H).

MS (EI) m/z: 493 (M$^+$), 167.

Example 26

Synthesis of 3-diphenylmethyl-4-((l)-menthyloxycarbonyl)-5-phenyl-2-oxazolidinone In 4 ml of methylene chloride were dissolved 0.405 g (1.0 mmol) of 3-diphenylmethyl-5-((l)-menthyloxy)-2(3H) oxazolone and 0.106 g (1.0 mmol) of benzaldehyde, and under argon atmosphere, the solution was cooled to −78° C., and TiCl$_4$ (19 mg: 0.1 mmol) was added to the solution and the mixture was reacted under stirring at the state for one hour and further at −20° C. for 2 hours.

Moreover, the temperature of the mixture was raised to the room temperature, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure, and the residue was applied to silica gel column chromatography (eluent: n-hexane/ethyl acetate=9/1) to obtain 0.24 g of a diastereomer mixture of a trans-isomer of 3-diphenylmethyl-4-((l)-menthyloxycarbonyl)-5-phenyl-2-oxazolidinone as white crystal. From $^1$H-NMR, a diastereomer ratio of the trans isomer was 64/36. Yield based on 3-diphenylmethyl-5-((l)-menthyloxy)-2(3H)oxazolone was 47%.

trans isomer (diastereomer mixture)

Melting point: 136 to 139° C.

IR (KBr, cm$^{-1}$): 1757 (s), 1390 (m).

$^1$H-NMR (δ, CDCl$_3$) (major isomer): 4.18 (d, J=3.7 Hz, 1H), 5.36 (d, J=3.7 Hz, 1H), 6.12 (s, 1H), (minor isomer): 4.15 (d, J=3.7 Hz, 1H), 5.39 (d, J=3.7 Hz, 1H), 6.18 (s, 1H).

MS (CI, i-C$_4$H$_{10}$) m/z: 512 (MH$^+$).

Example 27

Synthesis of 3-diphenylmethyl-4-((l)-menthyloxycarbonyl)-5-phenyl-2-oxazolidinone In 4 ml of methylene chloride were dissolved 0.405 g (1.0 mmol) of 3-diphenylmethyl-5-((l)-menthyloxy)-2(3H)oxazolone and 0.106 g (1.0 mmol) of benzaldehyde, and under argon atmosphere, the solution was cooled to −78° C., and BF$_3$.Et$_2$O (15 mg: 0.1 mmol) was added to the solution and the mixture was reacted under stirring at the state for 4 hours.

Moreover, the temperature of the mixture was raised to the room temperature, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. By adding 15 ml of methanol to the obtained residue, the material was crystallized to obtain 0.24 g of a diastereomer mixture of a trans-isomer of 3-diphenylmethyl-4-((l)-menthyloxycarbonyl)-5 -phenyl-2-oxazolidinone as white crystal. The selectivity was reversed to the case of Example 26, a diastereomer ratio of the formed product was 48/52. Yield based on 3-diphenylmethyl-5-((l)-menthyloxy)2(3H)oxazolone was 47%.

Example 28

Synthesis of 3-diphenylmethyl-4-((1S,2S,5R)-5-methyl-2-(1-methyl-1-phenylethyl)cyclohexyloxycarbonyl)-5-phenyl-2-oxazolidinone In 4 ml of methylene chloride were dissolved 3-diphenylmethyl-5-((1S,2S,5R)-5-methyl-2-(1-methyl-1-phenyl-ethyl)cyclohexyloxy)-2(3H)oxazolone (0.24 g; 0.5 mmol) and benzaldehyde (0.053 g; 0.5 mmol) of, and under argon atmosphere, the solution was cooled to −78° C., and 10 mg of BF$_3$.Et$_2$O was added to the solution and the mixture was reacted under stirring at −780° C. for 2 hours.

Moreover, the temperature of the mixture was raised to the room temperature, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. The material was crystallized to obtain 0.29 g of 3-diphenylmethyl-4-((1S,2S,5R)-5-methyl-2-(1-methyl-1-phenylethyl)cyclohexyloxycarbonyl)-5-phenyl-2-oxazolidinone as yellowish crystal. According to $^1$H-NMR analysis, a formation ratio of the cis/trans isomers of the formed product was 64/36. Also, a cis isomer and a trans isomer were obtained each as a single diastereomer, respectively. Yield based on 3-diphenylmethyl-5-((1S,2S,5R)-5-methyl-2-(1-methyl-1-phenylethyl)cyclohexyloxy)-2(3H) oxazolone was 99%.

cis isomer $^1$H-NMR (δ, CDC$_3$): 3.70 (d, J=9.8 Hz, 1H), 4.13 (td, J=3.90Hz, J=10.7 Hz, 1H), 5.24 (d, J=9.8 Hz, 1H), 5.91 (s, 1H).

trans isomer $^1$H-NMR (δ, CDCl$_3$): 3.50 (d, J=3.9 Hz, 1H), 4.73 (td, J=3.9 Hz, J=10.7 Hz, 1H), 5.07 (d, J=3.9 Hz, 1H), 5.97 (s, 1H).

MS (CI, i-C$_4$H$_{10}$) m/z: 588 (MH$^+$).

Example 29

Synthesis of 3-(1-(1-naphthyl)ethyl)-4-methoxycarbonyl-5-styryl-2-oxazolidinone

In 4 ml of methylene chloride were dissolved 0.135 g (0.5 mmol) of 3-(1-(1-naphthyl)ethyl)-5-methoxy-2(3H) oxazolone and 0.066 g (0.5 mmol) of cinnamaldehyde, and after cooling the solution to −78° C. under argon atmosphere, 10 mg of trimethylsilyl triflate was added to the solution and the mixture was reacted under stirring at that state for 2 hours.

Moreover, the temperature of the mixture was raised to the room temperature, and 15 ml of a saturated aqueous sodium hydrogen carbonate solution was added to the resulting reaction mixture and the mixture was extracted with 10 ml of methylene chloride. The organic layer was washed with a saturated salt solution, dried over anhydrous magnesium sulfate and concentrated under reduced pressure to obtain 3-(1-(1-naphthyl)ethyl)-4-methoxycarbonyl-5-styryl-2-oxazolidinone (0.20 g) as yellowish crystal. According to $^1$H-NMR, a formation ratio of cis/trans isomers of the formed product was 3/97 and a diastereomer ratio of the trans isomer was 92/8. Yield based on 3-(1-(1-naphthyl) ethyl)-5-methoxy-2(3H)oxazolone was 99%.

trans isomer (diastereomer mixture)

Melting point: 102 to 110 C.

IR (KBr, cm$^{-1}$): 1761 (s), 1683 (s), 1386 (s).

$^1$H-NMR (δ, CDCl$_3$) (major isomer): 1.81 (d, J=6.9 Hz, 3H), 3.14 (d, J=3.9 Hz, 1H), 3.74 (s, 3H), 4.81 (dd, J=3.9 Hz, J=6.8 Hz, 1H), 5.47 (dd, J=6.8 Hz, J=15.6 Hz, 1H), 5.96 (q, J=6.9 Hz, 1H), 6.40 (d, J=15.6 Hz, 1H), 6.9–8.0 (m, 12H).

MS (EI) m/z: 401 (M$^+$), 155.

Example 30

Synthesis of 3-diphenylmethyl-4-methoxycarbonyl-4-methyl-5-phenyl-2-oxazolidinone Under argon atmosphere, in 3 ml of methylene chloride was dissolved 148 mg (0.5 mmol) of 3-diphenylmethyl-4- methyl-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 191 mg (0.475 mmol) of 3-diphenylmethyl-4-methoxycarbonyl-4-methyl-5-phenyl-2-oxazolidinone as brownish oily substance. Yield based on 3-diphenylmethyl-4-methyl-5-methoxy-2(3H)oxazolone was 95%. According to the HPLC analysis, a formation ratio of the cis/trans isomers of the product was 10/90.

cis-trans isomers (mixture)

MS (CI, i-$C_4H_{10}$) m/z: 402 (MH$^+$).

trans isomer $^1$H-NMR (δ, CDCl$_3$): 0.91 (s, 3H), 3.44 (s, 3H), 5.52 (s, 1H), 5.65 (s, 1H), 7.14–7.33 (m, 15H).

$^{13}$C-NMR (δ, CDCl$_3$): 19.3, 52.9, 61.5, 68.8, 80.8, 126.3, 127.5, 127.7, 128.5, 128.6, 128.7, 129.0, 134.6, 138.6, 139.3, 155.9, 172.1.

cis isomer $^1$H-NMR (δ, CDCl$_3$): 1.51 (s, 3H), 2.84 (s, 3H), 5.20 (s, 1H), 5.68 (s, 1H), 7.14–7.33 (m, 15H).

$^{13}$C-NMR (δ, CDCl$_3$): 19.3, 52.9, 61.5, 68.8, 80.8, 126.3, 127.5, 127.7, 128.5, 128.6, 128.7, 129.0, 134.6, 138.6, 139.3, 155.9, 172.1.

Example 31

Synthesis of 3-diphenylmethyl-4-methoxycarbonyl-4-methyl-5-phenyl-2-oxazolidinone Under argon atmosphere, in 3 ml of methylene chloride was dissolved 148 mg (0.5 mmol) of 3-diphenylmethyl-4-methyl-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-t-butyldimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. When the obtained concentrated residue was quantitated by the HPLC method, yield of 3-diphenylmethyl-4-methoxycarbonyl-4-methyl-5-phenyl-2-oxazolidinone was 90%. According to the HPLC analysis, a formation ratio of cis/trans isomers of the formed product was 11/89.

Example 32

Synthesis of 3-diphenylmethyl-4-methoxycarbonyl-4-methyl-5-phenyl-2-oxazolidinone Under argon atmosphere, in 3 ml of methylene chloride was dissolved 148 mg (0.5 mmol) of 3-diphenylmethyl-4-methyl-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-TiCl$_4$ were added to the solution and the mixture was reacted under stirring for one hour.

Moreover, after the temperature of the mixture was raised up to the room temperature and stirring was carried out for further 18 hours, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. When the obtained concentrated residue was quantitated by the HPLC method, yield of 3-diphenylmethyl-4-methoxycarbonyl-4-methyl-5-phenyl-2-oxazolidinone was 59%. According to the HPLC analysis, a formation ratio of cis/trans isomers of the formed product was 20/80.

Example 33

Synthesis of 3-diphenylmethyl-4-methoxycarbonyl-4-methyl-5-phenyl-2-oxazolidinone Under argon atmosphere, in 3 ml of methylene chloride was dissolved 141 mg (0.5 mmol) of 3-diphenylmethyl-4-methyl-5-methoxy-2(3H)oxazolone, and after the solution was cooled to −78 C., 53.1 mg (0.5 mmol) of benzaldehyde and 0.05 ml (0.05 mmol) of a methylene chloride solution containing 1.0 M-BF$_3$.Et$_2$O were added to the solution and the mixture was reacted under stirring for one hour.

Moreover, after the temperature of the mixture was raised up to the room temperature and stirring was carried out for further 15 hours, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure. When the obtained concentrated residue was quantitated by the HPLC method, yield of 3-diphenylmethyl-4-methoxycarbonyl-4-methyl-5-phenyl-2-oxazolidinone was 43%. According to the HPLC analysis, a formation ratio of cis/trans isomers of the formed product was 31/69.

Example 34

Synthesis of 3-((R)-1-phenylethyl)-4-methoxycarbonyl-4-methyl-5-phenyl-2-oxazolidinone Under argon atmosphere, in 3 ml of methylene chloride was dissolved 117 mg (0.5 mmol) of 3-((R)-1-phenylethyl)-4-methyl-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 154 mg (0.455 mmol) of 3-((R)-1-phenylethyl)-4-methoxycarbonyl-4-methyl-5-phenyl-2-oxazolidinone as brownish oily substance. A diastereomer ratio of the formed product was (1):(2):(3):(4)=46:30:20:4. Yield based on 3-((R)-1-phenylethyl)-4-methyl-5-methoxy-2(3H) oxazolone was 91%.

diastereomer mixture

MS (CI, i-$C_4H_{10}$) m/z: 340 (MH$^+$).

Formed product (1) (trans isomer)

$^1$H-NMR ($\delta$, CDCl$_3$): 0.92 (s, 3H), 1.78 (d, J=7.3 Hz, 3H), 3.79 (s, 3H), 4.55 (q, J=7.3 Hz, 1H), 5.57 (s, 1H), 7.18–7.45 (m, 10H).

Formed product (2) (trans isomer)

$^1$H-NMR ($\delta$, CDCl$_3$): 0.95 (s, 3H), 1.89 (d, J=7.3 Hz, 3H), 3.57 (s, 3H), 4.67 (q, J=7.3 Hz, 1H), 5.62 (s, 1H), 7.18–7.45 (m, 10H).

Formed product (3) (cis isomer)

$^1$H-NMR ($\delta$, CDCl$_3$): 1.48 (s, 3H), 1.70 (d, J=7.8 Hz, 3H), 3.10 (s, 3H), 5.01 (q, J=7.8 Hz, 1H), 5.15 (s, 1H), 7.18–7.45 (m, 10H).

Formed product (4) (cis isomer)

$^1$H-NMR ($\delta$, CDCl$_3$): 1.54 (d, J=7.3 Hz, 3H), 1.60 (s, 3H), 3.17 (s, 3H), 4.90 (q, J=7.3 Hz, 1H), 5.17 (s, 1H), 7.18–7.45 (m, 10H).

Example 35

Synthesis of 3-((R)-1-phenylethyl)-4-methoxycarbonyl-4-methyl-5-phenyl-2-oxazolidinone Under argon atmosphere, in 3 ml of methylene chloride was dissolved 117 mg (0.5 mmol) of 3-((R)-1-phenylethyl)-4-methyl-5-methoxy-2(3H)oxazolone, and after the solution was cooled to −78° C., 53.1 mg (0.5 mmol) of benzaldehyde and 0.1 ml (0.1 mmol) of amethylene chloride solution containing 1.0 M-SnCl$_4$ were added to the solution and the mixture was reacted under stirring for one hour.

Moreover, after the temperature of the mixture was raised up to the room temperature and stirring was carried out further for 3 hours, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 74.7 mg (0.22 mmol) of 3-((R)-1-phenylethyl)-4-methoxycarbonyl-4-methyl-5-phenyl-2-oxazolidinone as brownish oily substance. A diastereomer ratio of the formed product was (1):(2):(3):(4)=42:13:39:6. Yield based on 3-((R)-1-phenylethyl)-4-methyl-5-methoxy-2(3H)oxazolone was 44%.

Example 36

Synthesis of 3-benzyl-4-methoxycarbonyl-4-methyl-5-phenyl-2-oxazolidinone

Under argon atmosphere, in 3 ml of methylene chloride was dissolved 110 mg (0.5 mmol) of 3-benzyl-4-methyl-5-methoxy-2(3H)oxazolone, and after the solution was cooled to −78° C., 53.1 mg (0.5 mmol) of benzaldehyde and 0.05 ml (0.05 mmol) of a methylene chloride solution containing 1.0 M-trimethylsilyl triflate were added to the solution and the mixture was reacted under stirring for one hour.

Moreover, after the temperature of the mixture was raised up to 0° C., 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 158 mg (0.485 mmol) of 3-benzyl-4-methoxycarbonyl-4-methyl-5-phenyl-2-oxazolidinone as brownish oily substance. Yield based on 3-benzyl-4-methyl-5-methoxy-2(3H)oxazolone was 97%. A formation ratio of the cis/trans isomers of the formed product was 59/41.

cis-trans isomers (mixture)

MS (CI, i-$C_4H_{10}$) m/z: 326 (MH$^+$).

$^1$H-NMR ($\delta$, CDCl$_3$) (trans isomer): 0.92 (s, 3H), 3.59 (s, 3H), 4.46 (d, J=15.6 Hz, 1H), 4.57 (d, J=15.6 Hz, 1H), 5.66 (s, 1H), 7.24–7.37 (m, 10H), (cis isomer): 1.53 (s, 3H), 3.14 (s, 3H), 4.08 (d, J=15.6 Hz, 1H), 4.77 (d, J=15.6 Hz, 1H), 5.21 (s, 1H), 7.24–7.37 (m, 10H).

Example 37

Synthesis of 3-benzyl-4-methoxycarbonyl-4-methyl-5-phenyl-2-oxazolidinone

Under argon atmosphere, in 3 ml of methylene chloride was dissolved 110 mg (0.5 mmol) of 3-benzyl-4-methyl-5-methoxy-2(3H)oxazolone, and after the solution was cooled to −78° C., 53.1 mg (0.5 mmol) of benzaldehyde and 0.1 ml (0.1 mmol) of a methylene chloride solution containing 1.0 M-SnCl$_4$ were added to the solution and the mixture was reacted under stirring for one hour.

Moreover, after the temperature of the mixture was raised up to the room temperature and stirring was carried out for 3 hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the obtained concentrated residue was quantitated by the HPLC method, yield of 3-benzyl-4-methoxycarbonyl-4-methyl-5-phenyl-2-oxazolidinone was 62%. A formation ratio of the cis/trans isomers of the formed product was 34/66.

Example 38

Synthesis of 4,5-anti-3-diphenylmethyl-4,5-dimethoxycarbonyl-2-oxazolidinone

Under argon atmosphere, in 2 ml of methylene chloride was dissolved 141 mg (0.5 mmol) of 3-diphenylmethyl-5-methoxy-2(3H)oxazolone, and after the solution was cooled to −78° C., 1 ml of a methylene chloride solution containing 0.5M methyl glyoxylate (44 mg (0.5 mmol) as methyl glyoxylate) and 0.05 ml (0.05 mmol) of a methylene chloride solution containing 1.0 M trimethylsilyl triflate were added to the solution and the mixture was reacted under stirring for one hour. Moreover, the temperature of the mixture was raised up to the room temperature and stirring was carried out for 15 hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. The residue was purified by silica gel column chromatography (n-hexane:ethyl acetate:methanol=5:1:1) to obtain 51.7 mg (0.14 mmol) of 4,5-anti-3-diphenylmethyl-4,5-dimethoxycarbonyl-2-oxazolidinone as colorless transparent oily substance. Yield based on 3-diphenylmethyl-5-methoxy-2(3H)-oxazolone was 28%.

MS (CI, i-$C_4H_{10}$) m/z: 370 (MH$^+$).

$^1$H-NMR (δ, $CDCl_3$): 3.38 (s, 3H), 3.86 (s, 3H), 4.40 (d, J=2.9 Hz, 1H), 4.83 (d, J=2.9 Hz, 1H), 5.65 (s, 1H), 6.24 (s, 1H), 7.20–7.36 (m, 10H).

Example 39

Synthesis of 4,5-anti-3-diphenylmethyl-4,5-dimethoxycarbonyl-2-oxazolidinone

Under argon atmosphere, in 2 ml of methylene chloride was dissolved 141 mg (0.5 mmol) of 3-diphenylmethyl-5-methoxy-2(3H)oxazolone, and after the solution was cooled to −78° C., 1 ml of a methylene chloride solution containing 0.5M methyl glyoxylate (44 mg (0.5 mmol)) and 0.05 ml (0.05 mmol) of a methylene chloride solution containing 1.0 M-$BF_3.Et_2O$ were added to the solution and the mixture was reacted under stirring for 2 hours.

Moreover, the temperature of the mixture was raised up to the room temperature and stirring was carried out for 16 hours, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the obtained concentrated residue was quantitated by the HPLC method, yield of 4,5-anti-3-diphenylmethyl-4,5-dimethoxycarbonyl-2-oxazolidinone was 47%.

Example 40

Synthesis of 4,5-anti-3-diphenylmethyl-4,5-dimethoxycarbonyl-2-oxazolidinone

Under argon atmosphere, in 2 ml of methylene chloride was dissolved 141 mg (0.5 mmol) of 3-diphenylmethyl-5-methoxy-2(3H)oxazolone, and after the solution was cooled to −78° C., 1 ml of a methylene chloride solution containing 0.5M methyl glyoxylate (44 mg (0.5 mmol)) and 0.05 ml (0.05 mmol) of a methylene chloride solution containing 1.0 M-$TiCl_4$ were added to the solution and the mixture was reacted under stirring for one hour.

Moreover, the temperature of the mixture was raised up to the room temperature and stirring was carried out for one hour, 15 ml of a saturated aqueous sodium hydrogen carbonate solution was added to the resulting reaction mixture and the mixture was extracted with 20 ml of methylene chloride. The organic layer was washed with 15 ml of a saturated aqueous sodium chloride solution, dried over anhydrous magnesium sulfate and concentrated under reduced pressure. When the obtained concentrated residue was quantitated by the HPLC method, yield of 4,5-anti-3-diphenylmethyl-4,5-dimethoxycarbonyl-2-oxazolidinone was 48%.

Example 41

Synthesis of 3-diphenylmethyl-4-methoxycarbonyl-5-(3,4-methylenedioxyphenyl)-2-oxazolidinone In 3 ml of methylene chloride was dissolved 141 mg (0.5 mmol) of 3-diphenylmethyl-5-methoxy-2(3H)oxazolone, and 75 mg (0.5 mmol) of 3,4-methylenedioxybenzaldehyde was added to the solution. After the solution was cooled to −78° C. under argon atmosphere, 5 ml (0.05 mmol) of a 0.1 N-methylene chloride solution containing $BF_3.Et_2O$ was added to the mixture and the mixture was reacted at that state under stirring for 30 minutes. Moreover, the temperature of the mixture was raised to 0° C. and the mixture was reacted under stirring for one hour.

Furthermore, the temperature of the mixture was raised up to around the room temperature, 15 ml of a saturated aqueous sodium hydrogen carbonate solution was added to the resulting reaction mixture and the mixture was extracted with 15 ml of methylene chloride. The organic layer was washed with a saturated aqueous sodium chloride solution, dried over anhydrous magnesium sulfate and concentrated under reduced pressure to obtain 180 mg of 3-diphenylmethyl-4-methoxycarbonyl-5-(3,4-methylenedioxyphenyl)-2-oxazolidinone as white crystal. According to the $^1$H-NMR analysis, no formation of a cis isomer was admitted. Yield based on 3-diphenylmethyl-5-methoxy-2(3H)oxazolone was substantially quantitative.

$^1$H-NMR (δ, $CDCl_3$) (trans isomer): 3.40 (s, 3H), 4.16 (d, J=3.9 Hz, 1H), 5.34 (d, J=3.9 Hz, 1H), 6.00 (s, 2H), 6.26 (s, 1H), 6.78 (m, 3H), 7.23–7.33 (m, 10H).

MS (EI) m/z: 431 (M$^+$), 206, 167.

Elemental analysis: Calcd: C, 69.60; H, 4.91; N, 3.25. Found: C, 69.50; H, 4.93; N, 3.20.

Example 42

Synthesis of 3-((R)-1-(1-naphthyl)ethyl)-4-methoxycarbonyl-5-(3,4-dimethoxyphenyl)-2-oxazolidinone In 3 ml of methylene chloride were dissolved 0.135 g (0.5 mmol) of 3-((R)-1-(1-naphthyl)ethyl)-5-methoxy-2(3H)oxazolone and 0.083 g (0.5 mmol) of 3,4-dimethoxybenzaldehyde, and after cooling the solution to −78° C. under argon atmosphere, 0.5 ml (0.05 mmol) of 0.1 N-methylene chloride solution of trimethylsilyl triflate was added to the solution and the mixture was reacted at that state under stirring for 30 minutes.

Moreover, the temperature of the mixture was raised up to around the room temperature, and 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure, and applied to silica gel column chromatography (eluent: n-hexane/ethyl acetate=4/1) to obtain 3-((R)-1-(1-naphthyl)ethyl)-4-methoxycarbonyl-5-(3,4-dimethoxyphenyl)-2-oxazolidinone as white crystal (0.19 g). A formation ratio of cis/trans isomers of the formed product was 2/98, and according to the $^1$H-NMR analysis, a diastereomer ratio of the trans isomer was 86/14. Yield based on 3-((R)-1-(1-naphthyl)ethyl)-5-methoxy-2(3H)oxazolone was 86%.

trans isomer (diastereomer mixture)

IR (KBr, cm$^{-1}$): 1755 (s), 1518 (m), 1399 (m).

$^1$H-NMR (δ, $CDCl_3$) (major isomer): 1.81 (d, J=6.8 Hz, 3H), 3.39 (d, J=5.4 Hz, 1H), 3.42 (s, 3H), 3.75 (s, 3H), 3.77 (s, 3H), 5.14 (d, J=5.4 Hz, 1H), 6.04 (q, J=6.8 Hz, 1H), 6.24 (d, J=2.0 Hz, 1H), 6.46 (dd, J=2.0 Hz, J=8.3 Hz, 1H), 6.54 (d, J=8.3 Hz, 1H), 7.38–7.55 (m, 4H), 7.83 (m, 2H), 8.04 (d, J=8.3 Hz, 1H).

MS (EI) m/z: 435 (M+), 222, 155.

Elemental analysis: Calcd: C, 65.98; H, 5.79; N, 3.22. Found: C, 68.66; H, 5.87; N, 3.30.

Example 43

Synthesis of 3-((R)-1-phenylethyl)-4-((l)-menthyloxycarbonyl)-5-phenyl-2-oxazolidinone Under argon atmosphere, in 3 ml of methylene chloride was dissolved 171.7 mg (0.5 mmol) of 3-((R)-1-phenylethyl)-5-((l)-menthyloxy)-2(3H)oxazolone, and after the solution was cooled to −78° C., 53.1 mg (0.5 mmol) of benzaldehyde and 0.5 ml (0.05 mmol) of a methylene chloride solution containing 0.1 M-trimethylsilyl triflate were added to the solution and the mixture was reacted under stirring for 30 minutes.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 211.5 mg (0.47 mmol) of 3-((R)-1-phenylethyl)-4-((l)-menthyloxycarbonyl)-5-phenyl-2-oxazolidinone as pale yellowish crystal. According to the $^1$H-NMR analysis, a formation ratio of the cis/trans isomers of the formed product was 6/94 and a diastereomer ratio of the trans isomer was 61/39. Yield based on 3-((R)-1-phenylethyl)-5-((l)-menthyloxy)-2(3H)oxazolone was 93%.

trans isomer (diastereomer mixture)

MS (CI, i-$C_4H_{10}$) m/z: 450 (MH+).

$^1$H-NMR ($\delta$, CDCl$_3$) (major isomer): 0.70–2.04 (m, 21H), 3.77 (d, J=4.4 Hz, 1H), 4.83 (ddd, J=4.4 Hz, 1H), 5.22 (d, J=4.4 Hz, 1H), 5.30 (q, J=6.8 Hz, 1H), 7.09–7.39 (m, 10H), (minor isomer): 0.70–2.04 (m, 21H), 4.09 (d, J=4.4 Hz, 1H), 4.61 (ddd, J=4.4 Hz, 1H), 4.93 (q, J=7.6 Hz, 1H), 5.29 (d, J=4.4 Hz, 1H), 7.09–7.39 (m, 10H).

Example 44

Synthesis of 3-((R)-1-phenylethyl)-4-((l)-menthyloxycarbonyl)-5-phenyl-2-oxazolidinone Under argon atmosphere, in 3 ml of methylene chloride was dissolved 171.7 mg (0.5 mmol) of 3-((R)-1-phenylethyl)-5-((l)-menthyloxy)-2(3H)oxazolone, and after the solution was cooled to −78° C., 53.1 mg (0.5 mmol) of benzaldehyde and 0.5 ml (0.05 mmol) of a methylene chloride solution containing 0.1 M-trimethylsilyl triflate were added to the solution and the mixture was reacted under stirring for one hour.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 209 mg (0.46 mmol) of 3-((R)-1-phenylethyl)-4-((l)-menthyloxycarbonyl)-5-phenyl-2-oxazolidinone as pale yellowish crystal. According to the $^1$H-NMR analysis, a formation ratio of the cis/trans isomers of the formed product was 14/86 and a diastereomer ratio of the trans isomer was 72/28. Yield based on 3-((R)-1-phenylethyl)-5-((l)-menthyloxy)-2(3H)oxazolone was 93%.

Example 45

Synthesis of 3-((S)-1-phenylethyl)-4-((l)-menthyloxycarbonyl)-5-phenyl-2-oxazolidinone Under argon atmosphere, in 3 ml of methylene chloride was dissolved 171.7 mg (0.5 mmol) of 3-((S)-1-phenylethyl)-5-((l)-menthyloxy)-2(3H)oxazolone, and after the solution was cooled to −78° C., 53.1 mg (0.5 mmol) of benzaldehyde and 0.5 ml (0.05 mmol) of a methylene chloride solution containing 0.1 M-trimethylsilyl triflate were added to the solution and the mixture was reacted under stirring for 30 minutes.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 207 mg (0.45 mmol) of 3-((S)-1-phenylethyl)-4-((l)-menthyloxycarbonyl)-5-phenyl-2-oxazolidinone as pale yellowish crystal. According to the $^1$H-NMR analysis, a diastereomer ratio of a trans isomer was 84/16. Yield based on 3-((S)-1-phenylethyl)-5-((l)-menthyloxy)-2(3H)oxazolone was 92%.

trans isomer (diastereomer mixture)

MS (CI, i-$C_4H_{10}$) m/z: 450 (MH+).

$^1$H-NMR ($\delta$, CDCl$_3$) (major isomer): 0.68–2.04 (m, 21H), 3.80 (d, J=4.4 Hz, 1H), 4.77 (ddd, J=4.4 Hz, 1H), 5.25 (d, J=4.4 Hz, 1H), 5.31 (q, J=6.8 Hz, 1H), 7.23–7.38 (m, 10H), (minor isomer): 0.68–2.04 (m, 21H), 4.1.(d, J=4.4 Hz, 1H), 4.58 (ddd, J=4.4 Hz, 1H), 4.95 (q, J=7.6 Hz, 1H), 5.29 (d, J=4.4 Hz, 1H), 7.23–7.38 (m, 10H).

Example 46

Synthesis of 3-((S)-1-phenylethyl)-4-((l)-menthyloxycarbonyl)-5-phenyl-2-oxazolidinone Under argon atmosphere, in 3 ml of methylene chloride was dissolved 171.7 mg (0.5 mmol) of 3-((S)-1-phenylethyl)-5-((l)-menthyloxy)-2(3H)oxazolone, and after the solution was cooled to −78° C., 53.1 mg (0.5 mmol) of benzaldehyde and 0.5 ml (0.05 mmol) of a methylene chloride solution containing 0.1 M boron trifluoride diethyl etherate were added to the solution and the mixture was reacted under stirring for one hour.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 199 mg (0.44 mmol) of 3-((S)-1-phenylethyl)-4-(l)-menthyloxycarbonyl-5-phenyl-2-oxazolidinone as pale yellowish crystal. According to the $^1$H-NMR analysis, a formation ratio of the cis/trans isomers of the formed product was 20/80 and a diastereomer ratio of the trans isomer was 70/30. Yield based on 3-((S)-1-phenylethyl)-5-((l)-menthyloxy)-2(3H)oxazolone was 89%.

Example 47

Synthesis of 3-((R)-1-(1-naphthyl)ethyl)-4-methoxycarbonyl-5-(3,4-methylenedioxyphenyl)-2-oxazolidinone Under argon atmosphere, in 3 ml of methylene chloride were dissolved 134.7 mg (0.5 mmol) of 3-((R)-1-(1- naphthyl)ethyl)-5-methoxy-2(3H)oxazolone and 75.1 mg (0.5 mmol) of 3,4-methylenedioxybenzaldehyde, and after the solution was cooled to −78° C., 0.5 ml (0.05 mmol) of a methylene chloride solution containing 0.1 M-trimethylsilyl triflate was added to the solution and the mixture was reacted under stirring for 2 hours.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure, and applied to silica gel column chromatography (eluent: n-hexane/ethyl acetate=5.5/1) to obtain 190.4 mg (0.44 mmol) of 3-((R)-1-(1-naphthyl)ethyl)-4-methoxycarbonyl-5-(3,4-methylenedioxyphenyl)-2-oxazolidinone as white crystal. According to the $^1$H-NMR analysis, no formation of a cis isomer was admitted and a diastereomer ratio of the trans isomer was 90/10. Yield based on 3-((R)-1-(1-naphthyl)ethyl)-5-methoxy-2(3H)oxazolone was 91%.

trans isomer (diastereomer mixture)

MS (EI) m/z: 419 (M$^+$), 155.

IR (KBr, cm$^{-1}$): 1757 (s), 1504 (m), 1399 (m).

Elemental analysis: Calcd: C, 68.73; H, 5.05; N, 3.34. Found: C, 68.09; H, 5.05; N, 3.34.

$^1$H-NMR (δ, CDCl$_3$) (major isomer): 1.82 (d, J=6.8 Hz, 3H), 3.22 (d, J=4.8 Hz, 1H), 3.72 (s, 3H), 5.09 (d, J=4.8 Hz, 1H), 5.84 (s, 2H), 5.99 (q, J=6.8 Hz, 1H), 6.23–7.97 (m, 10H), (minor isomer): 1.70 (d, J=6.8 Hz, 3H), 2.59 (s, 3H), 4.08 (d, J=4.8 Hz, 1H), 5.84 (s, 2H), 5.85 (d, J=4.8 Hz, 1H), 6.09 (q, J=6.8 Hz, 1H), 6.23–7.97 (m, 10H).

Example 48

Synthesis of 3-((R)-1-(1-naphthyl)ethyl)-4-methoxycarbonyl-5-(3,4-methylenedioxyphenyl)-2-oxazolidinone Under argon atmosphere, in 3 ml of methylene chloride were dissolved 134.7 mg (0.5 mmol) of 3-((R)-1-(1-naphthyl)ethyl)-5-methoxy-2(3H)oxazolone and 75.1 mg (0.5 mmol) of 3,4-methylenedioxybenzaldehyde, and after the solution was cooled to −78° C., 0.5 ml (0.05 mmol) of a methylene chloride solution containing 0.1 M-boron trifluoride diethyl etherate was added to the solution and the mixture was reacted under stirring for 2.5 hours.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 182.2 mg (0.43 mmol) of 3-((R)-1-(1-naphthyl)ethyl)-4-methoxycarbonyl-5-(3,4-methylenedioxyphenyl)-2-oxazolidinone as pale yellowish crystal. According to the $^1$H-NMR analysis, no formation of a cis isomer was admitted and a diastereomer ratio of the trans isomer was 79/21. Yield based on 3-((R)-1-(1-naphthyl)ethyl)-5-methoxy-2(3H)oxazolone was 87%.

Example 49

Synthesis of 3-((R)-1-(1-naphthyl)ethyl)-4-methoxycarbonyl-5-(3,4-methylenedioxyphenyl)-2-oxazolidinone Under argon atmosphere, in 3 ml of methylene chloride were dissolved 134.7 mg (0.5 mmol) of 3-((R)-1-(1-naphthyl)ethyl)-5-methoxy-2(3H)oxazolone and 75.1 mg (0.5 mmol) of 3,4-methylenedioxybenzaldehyde, and after the solution was cooled to −78° C., 0.5 ml (0.05 mmol) of a methylene chloride solution containing 0.1 M-t-butyldimethylsilyl trifluoromethanesulfonate was added to the solution and the mixture was reacted under stirring for 30 minutes.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, and dried over anhydrous magnesium sulfate and concentrated under reduced pressure to obtain 195.2 mg (0.47 mmol) of 3-((R)-1-(1-naphthyl)ethyl)-4-methoxycarbonyl-5-(3,4-methylenedioxyphenyl)-2-oxazolidinone as pale yellowish crystal. According to the $^1$H-NMR analysis, no formation of a cis isomer was admitted and a diastereomer ratio of the trans isomer was 88/12. Yield based on 3-((R)-1-(1-naphthyl)ethyl)-5-methoxy-2(3H)oxazolone was 93%.

Example 50

Synthesis of 3-((R)-1-(1-naphthyl)ethyl)-4-methoxycarbonyl-5-(3,4-methylenedioxyphenyl)-2-oxazolidinone Under argon atmosphere, in 3 ml of methylene chloride were dissolved 134.7 mg (0.5 mmol) of 3-((R)-1-(1-naphthyl)ethyl)-5-methoxy-2(3H)oxazolone and 75.1 mg (0.5 mmol) of 3,4-methylenedioxybenzaldehyde, and after the solution was cooled to −78° C., 0.5 ml (0.05 mmol) of a methylene chloride solution containing 0.1 M triisopropylsilyl trifluoromethanesulfonate was added to the solution and the mixture was raised and reacted at −20° C. for 1.5 hours.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, and dried over anhydrous magnesium sulfate and concentrated under reduced pressure to obtain 203.2 mg (0.48 mmol) of 3-((R)-1-(1-naphthyl)ethyl)-4-methoxycarbonyl-5-(3,4-methylenedioxyphenyl)-2-oxazolidinone as pale yellowish crystal. According to the $^1$H-NMR analysis, no formation of a cis isomer was admitted and a diastereomer ratio of the trans isomer was 75/25. Yield based on 3-((R)-1-(1-naphthyl)ethyl)-5-methoxy-2(3H)oxazolone was 97%.

Example 51

Synthesis of 3-((S)-1-phenylethyl)-4-((l)-menthyloxycarbonyl)-5-(3,4-methylenedioxyphenyl)-2-oxazolidinone Under argon atmosphere, in 3 ml of methylene chloride were dissolved 171.7 mg (0.5 mmol) of 3-((S)-1-phenylethyl)-5-((l)-menthyloxy)-2(3H)oxazolone and 75.1 mg (0.5 mmol) of 3,4-methylenedioxybenzaldehyde, and after the solution was cooled to −78° C., 0.5 ml (0.05 mmol) of a methylene chloride solution containing 0.1 M-trimethylsilyl triflate was added to the solution and the mixture was reacted under stirring for 30 minutes.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 214 mg (0.43 mmol) of 3-((S)-1-phenylethyl)-4-((l)-menthyloxycarbonyl)-5-(3,4-methylenedioxyphenyl)-2-oxazolidinone as pale yellowish viscous liquid. According to the $^1$H-NMR analysis, no formation of a cis isomer was admitted and a diastereomer ratio of a trans isomer was 70/30. Yield based on 3-((S)-1-phenylethyl)-5-((l)-menthyloxy)-2(3H)oxazolone was 87%.

trans isomer (diastereomer mixture)

MS (EI) m/z: 493 (M$^+$), 105.

$^1$H-NMR ($\delta$, CDCl$_3$) (major isomer): 0.65–2.04 (m, 21H), 3.75 (d, J=4.4 Hz, 1H), 4.76 (ddd, J=4.4 Hz, 1H), 5.14 (d, J=4.4 Hz, 1H), 5.32 (q, J=7.2 Hz, 1H), 5.94 (S, 1H), 6.45–7.41 (m, 9H), (minor isomer): 0.65–2.04 (m, 21H), 4.66 (d, J=4.4 Hz, 1H), 4.56 (ddd, J=4.4 Hz, 1H), 4.92 (q, J=7.2 Hz, 1H), 5.15 (d, J=4.4 Hz, 1H), 5.99 (S, 1H), 7.09–7.39 (m, 9H).

Example 52

Synthesis of 3-((S)-1-phenylethyl)-4-((l)-menthyloxycarbonyl)-5-(3,4-methylenedioxyphenyl)-2-oxazolidinone Under argon atmosphere, in 3 ml of methylene chloride were dissolved 171.7 mg (0.5 mmol) of 3-((S)-1-phenylethyl)-5-((l)-menthyloxy)-2(3H)oxazolone and 75.1 mg (0.5 mmol) of 3,4-methylenedioxybenzaldehyde, and after the solution was cooled to –78° C., 0.5 ml (0.05 mmol) of a methylene chloride solution containing 0.1 M triisopropylsilyl trifluoromethanesulfonate was added to the solution and the temperature of the mixture was raised to room temperature to react them under stirring for one hour.

Moreover, after the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 170.5 mg (0.35 mmol) of 3-((S)-1-phenylethyl)-4-((l)-menthyloxycarbonyl)-5-(3,4-methylenedioxyphenyl)-2-oxazolidinone as pale yellowish viscous liquid. According to the $^1$H-NMR analysis, a diastereomer ratio of a trans isomer was 51/49. Yield based on 3-((S)-1-phenylethyl)-5-((l)-menthyloxy)-2(3H)oxazolone was 69%.

Example 53

Synthesis of 3-phenyl-4-methyl-4-methoxycarbonyl-5-phenyl-2-oxazolidinone

Under argon atmosphere, in 3 ml of methylene chloride was dissolved 102.6 mg (0.5 mmol) of 3-phenyl-4-methyl-5-methoxy-2(3H)oxazolone, and after the solution was cooled to –78° C., 53.1 mg (0.5 mmol) of benzaldehyde and 0.5 ml (0.05 mmol) of a methylene chloride solution containing 0.1 M-trimethylsilyl triflate were added to the solution and the mixture was reacted under stirring for 1.0 hour. After the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure. The obtained concentrated residue was applied to silica gel column chromatography (eluent, hexane:ethyl acetate=10:1 (volume ratio)) to obtain 146.8 mg (0.47 mmol) of diastereomer mixture crude product of 3-phenyl-4-methyl-4-methoxycarbonyl-5-phenyl-2-oxazolidinone as pale yellowish liquid. A diastereomer ratio thereof was 72/28 according to $^1$H-NMR. Yield based on 3-phenyl-4-methyl-5-methoxy-2(3H)oxazolone was 94.3%.

(Mixture)

MS (EI) m/z: 311 (M$^+$), 252, 208, 118.

$^1$H-NMR ($\delta$, CDCl$_3$) (major isomer): 1.04 (s, 3H), 3.89 (s, 3H), 5.74 (s, 1H), 7.26–7.44 (m, 10H).

(minor isomer): 1.72 (s, 3H), 3.35 (s, 3H), 5.42 (s, 1H), 7.26–7.44 (m, 10H).

Example 54

Synthesis of 3-benzyl-5-((1S,2S,5R)-5-methyl-2-(1-methyl-1-phenylethyl)cyclohexyloxycarbonyl-5-isobutyl-2-oxazolidinone Under argon atmosphere, in 3 ml of methylene chloride was dissolved 202.8 mg (0.5 mmol) of 3-benzyl-5-((1S,2S,5R)-5-methyl-2-(1-methyl-1-phenylethyl)cyclohexyloxy)-2(3H)-oxazolone, and after the solution was cooled to –78° C., 36.1 mg (0.5 mmol) of isobutyl aldehyde and 63 $\mu$l (0.1 mmol) of boron trifluoride diethyl etherate were added to the solution and the mixture was reacted for 1.0 hour. After the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 232.1 mg (0.49 mmol) of a 4,5-trans isomer alone of 3-benzyl-5-((1S,2S,5R)-5methyl-2-(1-methyl-1-phenylethyl)cyclohexyloxycarbonyl-5-isobutyl-2-oxazolidinone as milky white viscous liquid. The obtained trans isomer was confirmed to be a single diastereomer according to $^1$H-NMR. Yield based on 3-benzyl-5-((1S,2S,5R)-5-methyl-2-(1-methyl-1-phenylethyl)cyclohexyloxy)-2(3H) oxazolone was 97.2%.

MS (CI, i-C$_4$H$_{10}$) m/z: 478 (MH$^+$).

$^1$H-NMR ($\delta$, CDCl$_3$): 0.62–2.01 (m, 25H), 2.95 (d, J=4.88 Hz, 1H), 3.82 (d, J=4.88 Hz, 1H), 4.18 (d, Jgem=15.13 Hz, 1H), 4.82 (ddd, J=3.91 lHz, 1H), 4.99 (d, Jgem=15.13 Hz, 1H), 6.82–7.45 (m, 10H)

Example 55

Synthesis of 3-benzyl-4-((1S,2S,5R)-5-methyl-2-(1-methyl-1-phenylethyl)cyclohexyloxycarbonyl-5-(2-phenylethyl)-2-oxazolidinone Under argon atmosphere, in 3 ml of methylene chloride was dissolved 202.8 mg (0.5 mmol) of 3-benzyl-5-((1S,2S, 5R)-5-methyl-2-(1-methyl-1-phenylethyl)cyclohexyloxy)-2 (3H)-oxazolone, and after the solution was cooled to –78° C., 67.1 mg (0.5 mmol) of hydrocinnamaldehyde and 63 $\mu$l (0.1 mmol) of boron trifluoride diethyl etherate were added to the solution and the mixture was reacted for 1.0 hour. After the temperature of the mixture was raised up to the room temperature, 15 ml of a saturated aqueous sodium hydrogen carbonate solution was added to the resulting reaction mixture and the mixture was extracted with 15 ml of methylene chloride. The organic layer was washed twice with 15 ml of water, dried over anhydrous magnesium sulfate and concentrated under reduced pressure to obtain 264.9 mg (0.49 mmol) of 3-benzyl-4-((1S,2S,5R)-5-methyl-2-(1-methyl-1-phenylethyl)cyclohexyloxy)carbonyl-5-(2-phenylethyl)-2-oxazolidinone as pale yellowish viscous liquid. A formation ratio of cis/trans isomers was cis isomer/trans isomer=29/71 according to $^1$H-NMR, and they were each single diastereomer. Yield based on 3-benzyl-5-((1S,2S,5R)-5-methyl-2-(1-methyl-1-phenylethyl)cyclohexyloxy)2(3H)oxazolone was 98.2%.

MS (CI, i-$C_4H_{10}$) m/z: 540 (MH$^+$).

$^1$H-NMR ($\delta$, CDCl$_3$): (trans isomer) 0.60–2.04 (m, 20H), 2.55–2.58 (m, 2H), 2.81 (d, J=5.86 Hz, 1H), 3.93 (d, J=5.86 Hz, 1H), 4.23 (d, Jgem=15.14 Hz, 1H), 4.74 (ddd, J=3.91 Hz, 1H), 4.98 (d, Jgem=15.14 Hz, 1H), 6.78–7.45 (m, 15H): (cis isomer) 0.60–2.04 (m, 20H), 2.58 (d, J=8.79 Hz, 1H), 3.22 (d, J=8.79 Hz, 1H), 3.75–4.13 (m, 2H), 4.08 (d, Jgem=15.14 Hz, 1H), 4.14 (ddd, J=3.91 Hz, 1H), 5.15 (d, Jgem=15.14 Hz, 1H), 6.78–7.45 (m, 15H).

Example 56

Synthesis of 3-diphenylmethyl-4-((1S,2S,5R)-5-methyl-2-(1-methyl-1-phenylethyl)cyclohexyloxycarbonyl)-5-phenyl-2-oxazolidinone In 4 ml of methylene chloride were dissolved of 3-diphenylmethyl-5-((1S,2S,5R)-5-methyl-2-(1-methyl-1-phenylethyl)cyclohexyloxy)-2(3H)oxazolone (0.24 g; 0.5 mmol) and benzaldehyde (0.053 g; 0.5 mmol), and after the solution was cooled to −78° C., 15 mg of triisopropylsilyl triflate was added to the solution and the mixture was reacted under stirring at −78° C. for 3 hours.

Moreover, after the temperature of the mixture was raised up to the room temperature, 15 ml of a saturated aqueous sodium hydrogen carbonate solution was added to the resulting reaction a mixture and the mixture was extracted with 20 ml of methylene chloride. The organic layer was washed with a saturated aqueous a sodium chloride solution, dried over anhydrous magnesium sulfate and concentrated under reduced pressure to obtain 0.30 g of 3-diphenylmethyl-4-((1S,2S,5R)-5-methyl-2-(1-methyl-1-phenylethyl)cyclohexyloxycarbonyl)-5-phenyl-2-oxazolidinone as yellowish crystal. According to the $^1$H-NMR analysis, a formation ratio of cis/trans isomers of the formed product was 74/26. Also, a cis isomer and a trans isomer were each obtained as a single diastereomer. Yield based on 3-diphenylmethyl-5-((1S,2S,5R)-5-methyl-2-(1-methyl-1-phenylethyl)cyclohexyloxy)-2(3H)-oxazolone was 99%.

The spectrum data were the same as those obtained in Example 28.

Example 57

Synthesis of 3-diphenymethyl-4-((1S,2S,5R)-5-methyl-2-(1-methyl-1-phenylethyl)cyclohexyloxycarbonyl)- 5-(2-phenylethyl)-2-oxazolidinone In 4 ml of methylene chloride were dissolved of 3-diphenylmethyl-5-((1S,2S,5R)-5-methyl-2-(1-methyl-1-phenylethyl)cyclohexyloxy)-2(3H)oxazolone (0.24 g; 0.5 mmol) and hydrocinnamaldehyde (0.067 g; 0.5 mmol), and after the solution was cooled to −78° C., 10 mg of BF$_3$.Et$_2$O was added to the solution and the mixture was reacted under stirring at −78° C. for 2 hours.

Moreover, after the temperature of the mixture was raised up to the room temperature, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 0.29 g of 3-diphenylmethyl-4-((1S,2S,5R)-5-methyl-2-(1-methyl-1-phenylethyl)cyclohexyloxycarbonyl)-5-(2-phenylethyl)-2-oxazolidinone as white crystal. According to the $^1$H-NMR analysis, a formation ratio of cis/trans isomers of the formed product was 13/87. Also, a cis isomer and a trans isomer were each obtained as a single diastereomer. Yield based on 3-diphenylmethyl-5-((1S,2S,5R)-5-methyl-2-(1-methyl-1-phenylethyl)cyclohexyloxy)-2(3H)oxazolone was 94%.

MS (EI) m/z: 615 (MH$^+$), 167.

cis isomer $^1$H-NMR ($\delta$, CDCl$_3$): 2.74–2.90 (m, 2H), 3.51 (d, J=8.3 Hz, 1H), 4.27 (m, 1H), 4.52 (td, J=3.9 Hz, J=10.7 Hz, 1H), 5.90 (s, 1H).

trans isomer $^1$H-NMR ($\delta$, CDCl$_3$): 2.50–2.71 (m, 2H), 3.06 (d, J=5.9 Hz, 1H), 3.91 (m, 1H), 4.61 (td, J=3.9 Hz, J=10.7 Hz, 1H), 5.88 (s, 1H).

Example 58

Synthesis of 3-diphenymethyl-4-((1S,2S,5R)-5-methyl-2-(1-methyl-1-phenylethyl)cyclohexyloxycarbonyl)-5-isopropyl-2-oxazolidinone In 4 ml of methylene chloride were dissolved of 3-diphenylmethyl-5-((1S,2S,5R)-5-methyl-2-(1-methyl-1-phenylethyl)cyclohexyloxy)-2(3H)oxazolone (0.24 g; 0.5 mmol) and isobutyl aldehyde (0.036 g; 0.5 mmol), and after the solution was cooled to −78° C., 10 mg of BF$_3$.Et$_2$O was added to the solution and the mixture was reacted under stirring at −78° C. for 5 hours.

Moreover, after the temperature of the mixture was raised up to the room temperature, 15 ml of a saturated aqueous sodium hydrogen carbonate solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 0.27 g of 3-diphenymethyl-4-((1S,2S,5R)-5-methyl-2-(1-methyl-1-phenylethyl)cyclohexyloxycarbonyl)-5-isopropyl-2-oxazolidinone as white crystal. According to the $^1$H-NMR analysis, a formation ratio of cis/trans isomers of the formed product was 81/19. Also, a cis isomer and a trans isomer were each obtained as a single diastereomer. Yield based on 3-diphenylmethyl-5-((1S,2S,5R)-5-methyl-2-(1-methyl-1-phenylethyl)cyclohexyloxy)-2(3H)oxazolone was 97%.

MS (EI) m/z: 553 (M+), 167.

cis isomer $^1$H-NMR ($\delta$, CDCl$_3$): 3.65 (d, J=7.3 Hz, 1H), 4.04 (t, J=7.3 Hz, 1H), 4.57 (td, J=10.7 Hz, J=3.9 Hz, 1H), 5.94 (s, 1H).

trans isomer $^1$H-NMR ($\delta$, CDCl$_3$): 3.23 (d, J=4.9 Hz, 1H), 3.86 (d, J=4.9 Hz, 1H), 4.76 (td, J=4.3 Hz, J=10.7 Hz, 1H), 5.78 (s, 1H).

Example 59

Synthesis of 3-diphenylmethyl-4-(1S,2S,5R)-5-methyl-2-(1-methyl-1-phenylethyl)cyclohexyloxycarbonyl)-5-phenyl-2-oxazolidinone In 4 ml of methylene chloride were dissolved of 3-diphenylmethyl-5-((1S,2S,5R)-5-methyl-2-(1-methyl-1- phenylethyl)cyclohexyloxy)-2(3H)oxazolone (0.24 g; 0.5 mmol) and benzaldehyde (0.053 g; 0.5 mmol), and after the solution was cooled to −78° C., 0.06 ml of a hexane solution containing 0.9 M diethyl aluminum chloride was added to the solution and the mixture was reacted under stirring at −78° C. for 2 hours.

Moreover, after the temperature of the mixture was raised up to the room temperature and the mixture was reacted for 3 hours, 15 ml of an aqueous 0.5N-hydrochloric acid solution was added to the resulting reaction mixture and the mixture was extracted with 20 ml of methylene chloride. The organic layer was washed with a saturated aqueous sodium chloride solution, dried over anhydrous magnesium sulfate and concentrated under reduced pressure to obtain 0.27 g of 3-diphenylmethyl-4-((1S,2S,5R)-5-methyl-2-(1-methyl-1-phenylethyl)cyclohexyloxycarbonyl)-5-phenyl-2-oxazolidinone as white crystal. According to the $^1$H-NMR analysis, a formation ratio of cis/trans isomers of the formed product was 74/26. Also, a cis isomer and a trans isomer were each obtained as a single diastereomer. Yield based on 3-diphenylmethyl-5-((1S,2S,5R)-5-methyl-2-(1-methyl-1-phenylethyl)cyclohexyloxy)-2(3H)oxazolone was 90%.

The spectrum data were the same as those obtained in Example 28.

UTILIZABILITY IN INDUSTRY

According to the present invention, a 4-alkoxycarbonyl-2-oxazolidinone compound can be obtained by reacting 5-alkoxy-2(3H)oxazolone compound and an aldehyde compound in the presence of a Lewis acid catalyst. The obtained 4-alkoxycarbonyl-2-oxazolidinone compound is useful as a starting material of a β-hydroxy-α-amino acid compound which has been used as a drug matter, an intermediate or a starting material.

What is claimed is:

1. A process for producing a 4-alkoxycarbonyl-2-oxazolidinone compound represented by the formula (III):

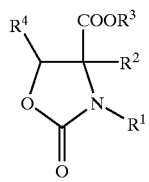

(III)

wherein $R^1$ represents a hydrogen atom, a substituted or unsubstituted $C_1$ to $C_{10}$ alkyl group, a substituted or unsubstituted $C_3$ to $C_{10}$ cycloalkyl group, a substituted or unsubstituted $C_2$ to $C_{10}$ alkenyl group or a substituted or unsubstituted phenyl group, $R^2$ represents a hydrogen atom, a substituted or unsubstituted $C_1$ to $C_{10}$ alkyl group, a substituted or unsubstituted phenyl group or a $C_2$ to $C_{10}$ alkenyl group which is not substituted, $R^3$ represents a substituted or unsubstituted $C_1$ to $C_{10}$ alkyl group, a substituted or unsubstituted $C_3$ to $C_{10}$ cycloalkyl group, an unsubstituted or, provided that a 2-alkenyl group is excluded, substituted $C_2$ to $C_{10}$ alkenyl group, or a substituted or unsubstituted phenyl group, and $R^4$ represents a hydrogen atom, a substituted or unsubstituted $C_1$ to $C_{20}$ alkyl group, a substituted or unsubstituted $C_2$ to $C_{20}$ alkenyl group, a substituted or unsubstituted $C_3$ to $C_{10}$ cycloalkyl group, a substituted or unsubstituted $C_2$ to $C_{20}$ alkynyl group, a substituted or unsubstituted $C_6$ to $C_{20}$ aryl group, a substituted or unsubstituted 5- or 6-membered heteroaromatic ring group having 1 or 2 hetero atoms selected from N, O and S, a substituted or unsubstituted $C_1$ to $C_6$ alkoxycarbonyl group, an acetyl group or a benzoyl group, which comprises reacting a 5alkoxy-2(3H)oxazolone compound represented by the formula (I):

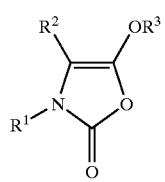

(I)

wherein $R^1$, $R^2$ and $R^3$ have the same meanings as defined above, and an aldehyde compound represented by the formula (II):

$R^4CHO$ (II)

wherein $R^4$ has the same meaning as defined above, in the presence of a Lewis acid catalyst.

2. The method according to claim 1, wherein the Lewis acid is a halide or a trifluoromethane sulfonate of an element from Group 2 to Group 4 of the Periodic Table, or a Lanthanoid group metal.

3. The method according to claim 1, wherein the Lewis acid is a compound represented by the formula (IV):

(IV)

wherein $R^5$ represents a $C_1$ to $C_{10}$ alkyl group or a $C_6$ to $C_{20}$ aryl group; X represents a halogen atom; M represents Al, B, Sn or Ti; m and n each represents a number of 0, 1, 2, 3 or 4; provided that m+n is 2, 3 or 4.

4. The method according to claim 1, wherein the Lewis acid is a compound represented by the formula (V):

(V)

wherein $R^6$ represents a $C_1$ to $C_{10}$ alkyl group or a $C_6$ to $C_{20}$ aryl group; X represents a halogen atom; M represents Al, B, Sn or Ti; m' and n' each represents a number of 0, 1, 2, 3 or 4; provided that m'+n' is 3 or 4.

5. The method according to claim 1, wherein the Lewis acid is a compound represented by the formula (VI):

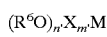

(VI)

wherein $R^7$, $R^8$ and $R^9$ each independently represents a $C_1$ to $C_{10}$ alkyl group or a $C_6$ to $C_{20}$ aryl group; X' represents a halogen atom or —$OSO_2CF_3$.

6. The method according to claim 1, wherein the Lewis acid is aluminum (III) chloride, aluminum (III) bromide, aluminum (III) iodide, diethyl aluminum chloride, ethyl aluminum dichloride, trimethyl aluminum, triethyl aluminum, triisopropyl aluminum, tributyl aluminum, aluminum (III) isopropoxide, boron trichloride, boron trifluoride, boron trifluoride diethyl etherate, boron tribromide, triphenoxyborane, phenyl dichloroborane, tin (IV) chloride, tin (IV) bromide, tin (II) chloride, tin (II) triflate, titanium (IV) chloride, titanium (IV) fluoride, titanium (IV) bromide, titanium (IV) iodide, dichloroisopropoxy titanium, titanium (IV) isopropoxide, zinc (II) chloride, zinc (II) bromide, iron (II) chloride, iron (III) chloride, magnesium chloride, ytterbium (III) triflate, samarium iodide, samarium (III) triflate, trimethylsilyl triflate, trimethylsilyl iodide, tert-butyldimethylsilyl triflate or triisopropylsilyl triflate.

7. The method according to claim 1, wherein the compound represented by the formula (I) is 3-benzyl-5-(l)-menthyloxy-2(3H)oxazolone, 3-benzyl-5-((1S,2S,5R)-5-methyl-2-(1-methyl-1-phenylethyl)cyclohexyloxy)-2(3H)oxazolone, 3-(4-methylbenzyl)-4-methyl-5-methoxy-2(3H)oxazolone, 3-(1-phenylethyl)-5-methoxy-2(3H)oxazolone, 3-((S)-1-phenylethyl)-5-isopropoxy-2(3H)oxazolone, 3-((R)-1-phenylethyl)-5-methoxy-2(3H)oxazolone, 3-diphenylmethyl-5-methoxy-2(3H)oxazolone, 3-diphenylmethyl-5-(l)-menthyloxy-2(3H)oxazolone, 3-diphenylmethyl-5-((1S,2S,5R)-5-methyl-2-(1-methyl-1-phenylethyl)cyclohexyloxy)-2(3H)oxazolone, 3-((R)-1-(1-naphthyl)ethyl)-5-methoxy-2(3H)oxazolone, 3-furfuryl-4-ethyl-5-methoxy-2(3H)oxazolone, 3-furfuryl-4-ethyl-5-(4-pentenyl)oxy-2(3H)-oxazolone, 3-isopropyl-5-methoxy-2(3H)oxazolone, 3-benzyl-5-methoxy-2(3H)oxazolone, 3-isopropyl-4-methyl-5-methoxy-2(3H)oxazolone, 3-isopropyl-4-methyl-5-ethoxy-2(3H)oxazolone, 3-isopropyl-4-methyl-5-cyclohexyloxy-2(3H)oxazolone, 3-((R)-1-(1-naphthyl)ethyl)-5-isopropoxy-2(3H)oxazolone, 3-((R)-1-phenylethyl)-4-methyl-5-methoxy-2(3H)oxazolone, 3-((S)-1-phenylethyl)-5-phenoxy-2(3H)oxazolone, 3-benzyl-4-methyl-5-methoxy-2(3H)oxazolone, 3-(1-naphthyl)methyl-5-methoxy-2(3H)oxazolone, 3-((R)-1-phenylethyl)-5-(l)-menthyloxy-2(3H)-oxazolone, 3-((S)-1-phenylethyl)-5-(l)-menthyloxy-2(3H)oxazolone or 3-phenyl-4-methyl-5-methoxy-2(3H)oxazolone.

8. The method according to claim 1, wherein the compound represented by the formula (II) is benzaldehyde, 4-methoxybenzaldehyde, 2-methoxybenzaldehyde, 3,4-methylenedioxybenzaldehyde, 3,4-dimethoxybenzaldehyde, 4-nitrobenzaldehyde, 2-nitrobenzaldehyde, naphthylaldehyde, acetaldehyde, propionaldehyde, n-butylaldehyde, isobutyl aldehyde, cinnamaldehyde, hydrocinnamaldehyde, crotonaldehyde, phenylacetaldehyde, α-benzyloxypropionaldehyde, methylglycidiate, acrolein, tetradecenal, or benzyloxyacetaldehyde.

* * * * *